(12) United States Patent
Mercer et al.

(10) Patent No.: US 10,702,649 B2
(45) Date of Patent: Jul. 7, 2020

(54) COMBINATION FLUID INSTILLATION AND NEGATIVE PRESSURE DRESSING

(71) Applicant: KCI Licensing, Inc., San Antonio, TX (US)

(72) Inventors: David Richard Mercer, San Antonio, TX (US); Christopher Brian Locke, Bournemouth (GB); Benjamin Andrew Pratt, Poole (GB)

(73) Assignee: KCI Licensing, Inc., San Antonio, TX (US)

(*) Notice: Subject to any disclaimer, the term of this patent is extended or adjusted under 35 U.S.C. 154(b) by 453 days.

(21) Appl. No.: 15/328,415

(22) PCT Filed: Jul. 24, 2015

(86) PCT No.: PCT/US2015/042097
§ 371 (c)(1),
(2) Date: Jan. 23, 2017

(87) PCT Pub. No.: WO2016/015001
PCT Pub. Date: Jan. 28, 2016

(65) Prior Publication Data
US 2017/0209641 A1    Jul. 27, 2017

Related U.S. Application Data

(60) Provisional application No. 62/028,672, filed on Jul. 24, 2014.

(51) Int. Cl.
*A61M 1/00* (2006.01)
*A61M 3/02* (2006.01)

(52) U.S. Cl.
CPC ........ *A61M 3/0283* (2013.01); *A61M 1/0058* (2013.01); *A61M 1/0084* (2013.01);
(Continued)

(58) Field of Classification Search
CPC . A61M 1/0058; A61M 1/0088; A61M 3/0283
See application file for complete search history.

(56) References Cited

U.S. PATENT DOCUMENTS

| 1,355,846 A | 10/1920 | Rannells |
| 2,547,758 A | 4/1951 | Keeling |

(Continued)

FOREIGN PATENT DOCUMENTS

| AU | 550575 B2 | 3/1986 |
| AU | 745271 B2 | 3/2002 |

(Continued)

OTHER PUBLICATIONS

Louis C. Argenta, MD and Michael J. Morykwas, PHD; Vacuum-Assisted Closure; A New Method for Wound Control and Treatment: Clinical Experience; Annals of Plastic Surgery.

(Continued)

*Primary Examiner* — Adam Marcetich
*Assistant Examiner* — Jessica R Arble

(57) ABSTRACT

Some illustrative embodiments of an instillation assembly for treating a tissue site may include a fluid distribution lumen and a fluid hub that may define a fluid instillation pathway. The fluid distribution lumen may be defined by a first film layer and a second film layer, and the fluid hub may be positioned in fluid communication with the fluid distribution lumen. The installation assembly may be used in combination with a reduced-pressure assembly that may define a reduced-pressure pathway separate from the fluid instillation pathway.

25 Claims, 10 Drawing Sheets

(52) U.S. Cl.
CPC ........ *A61M 1/0088* (2013.01); *A61M 3/0254* (2013.01); *A61M 2205/15* (2013.01); *A61M 2205/18* (2013.01); *A61M 2205/583* (2013.01); *A61M 2205/8206* (2013.01); *A61M 2207/00* (2013.01); *A61M 2210/1021* (2013.01)

(56) References Cited

U.S. PATENT DOCUMENTS

| | | |
|---|---|---|
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielsen |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,645,081 A | 7/1997 | Argenta et al. |
| 6,071,267 A | 6/2000 | Zamierowski |
| 6,135,116 A | 10/2000 | Vogel et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,814,079 B2 | 11/2004 | Heaton et al. |
| 7,276,051 B1 | 10/2007 | Henley et al. |
| 7,846,141 B2 | 12/2010 | Weston |
| 8,062,273 B2 | 11/2011 | Weston |
| 8,216,198 B2 | 7/2012 | Heagle et al. |
| 8,251,979 B2 | 8/2012 | Malhi |
| 8,257,327 B2 | 9/2012 | Blott et al. |
| 8,398,614 B2 | 3/2013 | Blott et al. |
| 8,449,509 B2 | 5/2013 | Weston |
| 8,529,548 B2 | 9/2013 | Blott et al. |
| 8,535,296 B2 | 9/2013 | Blott et al. |
| 8,551,060 B2 | 10/2013 | Schuessler et al. |
| 8,568,386 B2 | 10/2013 | Malhi |
| 8,679,081 B2 | 3/2014 | Heagle et al. |
| 8,834,451 B2 | 9/2014 | Blott et al. |
| 8,926,592 B2 | 1/2015 | Blott et al. |
| 9,017,302 B2 | 4/2015 | Vitaris et al. |
| 9,198,801 B2 | 12/2015 | Weston |
| 9,211,365 B2 | 12/2015 | Weston |
| 9,289,542 B2 | 3/2016 | Blott et al. |
| 2002/0077661 A1 | 6/2002 | Saadat |
| 2002/0115951 A1 | 8/2002 | Norstrem et al. |
| 2002/0120185 A1 | 8/2002 | Johnson |
| 2002/0143286 A1 | 10/2002 | Tumey |
| 2002/0150720 A1 | 10/2002 | Howard et al. |
| 2006/0155260 A1* | 7/2006 | Blott .................. A61M 3/0212 604/543 |
| 2011/0009839 A1* | 1/2011 | Lu ..................... A61F 13/00068 604/319 |
| 2011/0213320 A1* | 9/2011 | Blott ..................... A61M 35/00 604/313 |
| 2011/0224630 A1* | 9/2011 | Simmons ............ A61M 1/0088 604/317 |
| 2011/0257611 A1* | 10/2011 | Locke ................ A61F 13/0203 604/319 |
| 2012/0077886 A1* | 3/2012 | Scholz .................... A61L 15/24 514/772.4 |
| 2013/0165821 A1* | 6/2013 | Freedman ......... A61F 13/00063 601/2 |
| 2013/0178785 A1* | 7/2013 | Papay .................... A61N 1/325 604/20 |
| 2014/0163491 A1 | 6/2014 | Schuessler et al. |
| 2015/0080788 A1 | 3/2015 | Blott et al. |

FOREIGN PATENT DOCUMENTS

| | | |
|---|---|---|
| AU | 755496 B2 | 12/2002 |
| CA | 2005436 A1 | 6/1990 |
| DE | 26 40 413 A1 | 3/1978 |

(56) References Cited

FOREIGN PATENT DOCUMENTS

| | | |
|---|---|---|
| DE | 43 06 478 A1 | 9/1994 |
| DE | 29 504 378 U1 | 9/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 A1 | 7/2000 |
| EP | 1742684 A1 | 1/2007 |
| GB | 692578 A | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 A | 3/1999 |
| GB | 2 333 965 A | 8/1999 |
| JP | 4129536 B2 | 8/2008 |
| SG | 71559 | 4/2002 |
| WO | 80/02182 A1 | 10/1980 |
| WO | 87/04626 A1 | 8/1987 |
| WO | 90/010424 A1 | 9/1990 |
| WO | 93/009727 A1 | 5/1993 |
| WO | 94/020041 A1 | 9/1994 |
| WO | 96/05873 A1 | 2/1996 |
| WO | 97/18007 A1 | 5/1997 |
| WO | 99/13793 A1 | 3/1999 |
| WO | 0007653 A1 | 2/2000 |
| WO | 2005046762 A1 | 5/2005 |
| WO | 2005105180 A1 | 11/2005 |
| WO | 2011130551 A1 | 10/2011 |
| WO | 2013066694 A2 | 5/2013 |

OTHER PUBLICATIONS

Susan Mendez-Eatmen, RN; "When wounds Won't Heal" RN Jan. 1998, vol. 61 (1); Medical Economics Company, Inc., Montvale, NJ, USA; pp. 20-24

James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.

John Masters; "Reliable, Inexpensive and Simple Suction Dressings"; Letter to the Editor, British Journal of Plastic Surgery, 198, vol. 51 (3), p. 267; Elsevier Science/The British Association of Plastic Surgeons, UK.

S.E. Greer, et al. "The Use of Subatmospheric Pressure Dressing Therapy to Close Lymphocutaneous Fistulas of the Groin" British Journal of Plastic Surgery (2000), 53, pp. 484-487.

George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.

Orringer, Jay, et al; "Management of Wounds in Patients with Complex Enterocutaneous Fistulas"; Surgery, Gynecology & Obstetrics, Jul. 1987, vol. 165, pp. 79-80

International Search Report for PCT International Application PCT/GB95/01983; dated Nov. 23, 1995.

PCT International Search Report for PCT International Application PCT/GB98/02713; dated Jan. 8, 1999.

PCT Written Opinion; PCT International Application PCT/GB98/02713; dated Jun. 8, 1999.

PCT International Examination and Search Report, PCT International Application PCT/GB96/02802; dated Jan, 15, 1998 & Apr. 29, 1997.

PCT Written Opinion, PCT International Application PCT/GB96/02802; dated Sep. 3, 1997.

Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.

Kostyuchenok, B.M., et al; "Vacuum Treatment in the Surgical Management of Purulent Wounds"; Vestnik Khirurgi, Sep. 1986, pp. 18-21 and 6 page English translation thereof.

Davydov, Yu. A., et al; "Vacuum Therapy in the Treatment of Purulent Lactation Mastitis"; Vestnik Khirurgi, May 14, 1986, pp. 66-70, and 9 page English translation thereof.

Yusupov, Yu.N., et al; "Active Wound Drainage", Vestnki Khirurgi, vol. 138, Issue 4, 1987, and 7 page English translation thereof.

Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.

Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E., M.D., et al; "Effective Management of incisional and cutaneous fistulae with closed suction wound drainage"; Contemporary Surgery, vol. 34, Jun. 1989, pp. 59-63.

Egnell Minor, Instruction Book, First Edition, 300 7502, Feb. 1975, pp. 24.

Egnell Minor: Addition to the Users Manual Concerning Overflow Protection—Concerns all Egnell Pumps, Feb. 3, 1983, pp. 2.

Svedman, P.: "Irrigation Treatment of Leg Ulcers", The Lancet, Sep. 3, 1983, pp. 532-534.

Chinn, Steven D. et al.: "Closed Wound Suction Drainage", The Journal of Foot Surgery, vol. 24, No. 1, 1985, pp. 76-81.

Arnljots, Björn et al.: "Irrigation Treatment in Split-Thickness Skin Grafting of Intractable Leg Ulcers", Scand J. Plast Reconstr. Surg., No. 19, 1985, pp. 211-213.

Svedman, P.: "A Dressing Allowing Continuous Treatment of a Biosurface", IRCS Medical Science: Biomedical Technology, Clinical Medicine, Surgery and Transplantation, vol. 7, 1979, p. 221.

Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.

N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (copy and certified translation).

K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.

G. Živadinovi?, V. ?uki?, Ž. Maksimovi?, ?. Radek, and P. Peška, "Vacuum Therapy in the Treatment of Peripheral Blood Vessels," Timok Medical Journal 11 (1986), pp. 161-164 (copy and certified translation).

F.E. Johnson, "An Improved Technique for Skin Graft Placement Using a Suction Drain," Surgery, Gynecology, and Obstetrics 159 (1984), pp. 584-585.

A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).

M. Schein, R. Saadia, J.R. Jamieson, and G.A.G, Decker, "The 'Sandwich Technique' in the Management of the Open Abdomen," British Journal of Surgery 73 (1986), pp. 369-370.

D.E. Tribble, An Improved Sump Drain-Irrigation Device of Simple Construction, Archives of Surgery 105 (1972) pp. 511-513.

M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).

C.E. Tennants, "The Use of Hypermia in the Postoperative Treatment of Lesions of the Extremities and Thorax, " Journal of the American Medical Association 64 (1915), pp. 1548-1549.

Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.

V.A. Solovev et al., Guidelines, the Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").

(56) References Cited

OTHER PUBLICATIONS

V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract")
V.A.C.® Therapy Clinical Guidelines: A Reference Source for Clinicians; Jul. 2007.
Chinese First Office Action for Corresponding Application No. 2015800478463, dated Sep. 18, 2018.
Japanese Notice of Rejection Corresponding to Application No. 2017503568, dated Jun. 4, 2019.
International Search Report and Written Opinion for Corresponding Application No. PCT/US2015/042097, dated Jan. 22, 2016.
Extended European Search Report for Corresponding Application No. 182152264, dated Apr. 10, 2019.

\* cited by examiner

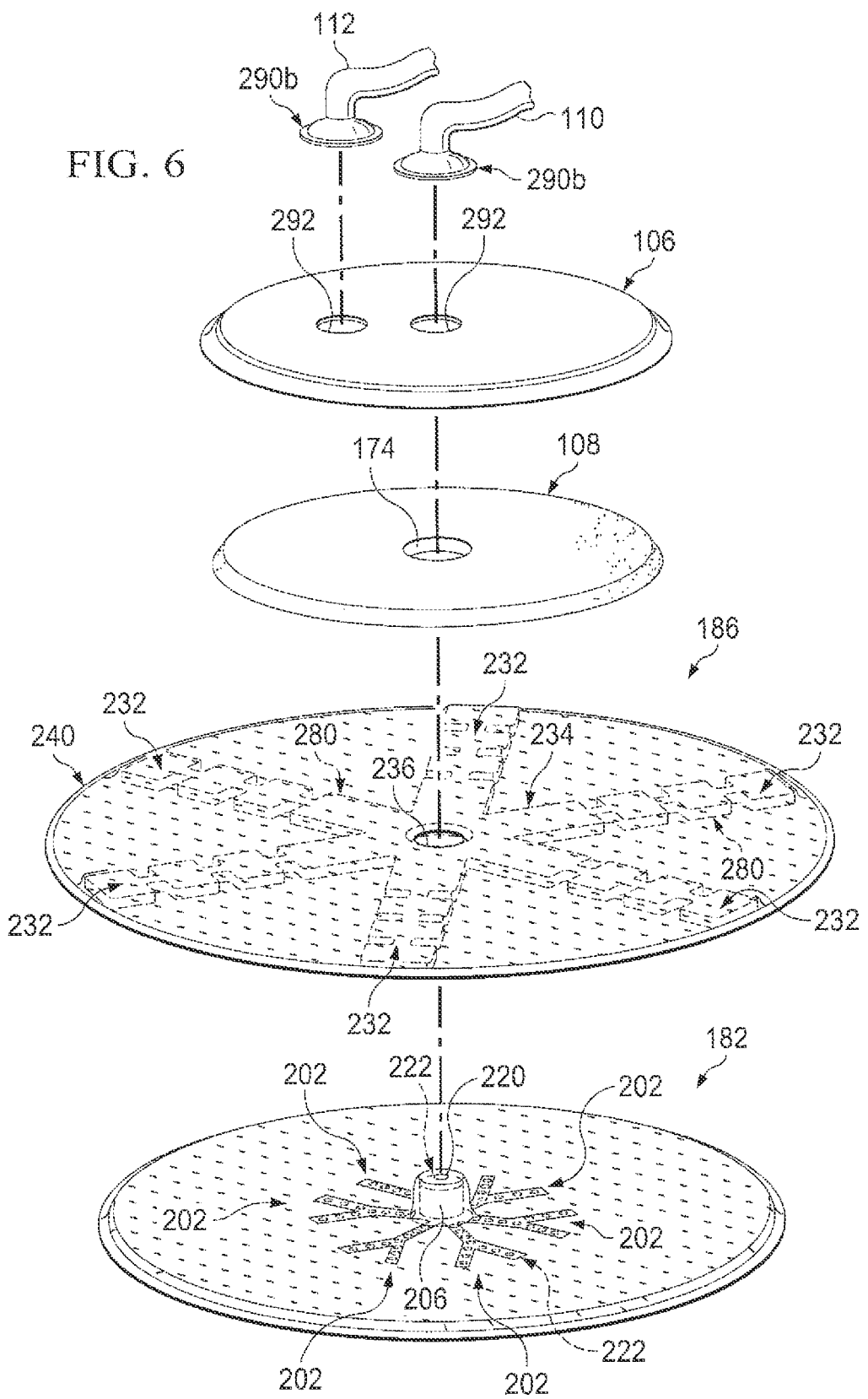

COMBINATION FLUID INSTILLATION AND NEGATIVE PRESSURE DRESSING

RELATED APPLICATION

This application claims the benefit, under 35 USC § 119(e), of the filing of U.S. Provisional Patent Application No. 62/028,672, entitled "Combination Fluid Installation and Negative Pressure Dressing," filed Jul. 24, 2014, which is incorporated herein by reference for all purposes.

FIELD

This disclosure relates generally to medical treatment systems and, more particularly, but not by way of limitation, to systems, dressings, devices, and methods suitable for treating a tissue site.

BACKGROUND

Depending on the medical circumstances, reduced pressure may be used for, among other things, reduced-pressure therapy to encourage granulation at a tissue site, draining fluids at a tissue site, closing a wound, reducing edema, promoting perfusion, and fluid management. Further, therapeutic fluids may be instilled or distributed to a tissue site in combination with or in lieu of reduced-pressure therapy. The instillation of such fluids to a tissue site may assist with preventing infection, enhancing healing, and other therapeutic benefits.

Challenges can exist with distributing fluids to and extracting fluids from a tissue site being subjected to reduced-pressure therapy or fluid instillation. For example, tissue sites may vary in volume, size, geometry, orientation, and other factors. Further, access to these tissue sites may be restricted. These and other factors can make extraction of waste fluids from the tissue site and distribution of therapeutic fluids to the tissue site difficult to perform in a uniform or even manner. Further, directional changes in fluid flow between reduced-pressure therapy cycles and instillation fluid cycles can force waste fluids being extracted during a reduced-pressure therapy cycle back into a tissue site upon switching to a fluid instillation cycle.

Types of tissue sites that may present particular difficulties may include locations such as a peritoneal cavity, and more generally, an abdominal cavity. When a tissue site involves the abdominal cavity, a treatment system that may allow for improved and efficient care, and may address such complications as peritonitis, abdominal compartment syndrome, and infections that might inhibit final healing may be particularly beneficial. Thus, improvements to treatment systems that may adapt to various types of tissue sites and orientations, enhance the uniformity of waste fluid extraction and therapeutic fluid distribution, and increase efficiency and healing times may be desirable.

SUMMARY

Shortcomings with certain aspects of tissue treatment systems, dressings, devices, and methods are addressed as shown and described in a variety of illustrative, non-limiting embodiments herein.

In some embodiments, a treatment system for providing fluid instillation and reduced pressure treatment at a tissue site may include a plurality of fluid distribution lumens, a fluid hub, a plurality of leg members, a reduced-pressure hub, a fluid supply lumen, and a reduced-pressure lumen. The plurality of fluid distribution lumens may be defined between a first film layer and a second film layer. Each of the fluid distribution lumens may have a delivery aperture in fluid communication with the fluid distribution lumen. The fluid hub may be positioned in fluid communication with the plurality of fluid distribution lumens. Further, the fluid hub and the plurality of fluid distribution lumens may define a fluid instillation pathway. Each leg member of the plurality of leg members may include a leg manifold. The reduced-pressure hub may be in fluid communication with the plurality of leg members. Further, the reduced-pressure hub and the plurality of leg members may define a reduced-pressure pathway separate from the fluid instillation pathway. The fluid supply lumen may be adapted to be coupled in fluid communication with the fluid hub, and the reduced-pressure lumen may be adapted to be coupled in fluid communication with the reduced-pressure hub.

In some embodiments, an instillation assembly for treating a tissue site may include a fluid distribution lumen and a fluid hub. The fluid distribution lumen may have a length and opposing sides positioned normal to the length. The fluid distribution lumen may be defined by a first film layer and a second film layer. The first film layer may be sealingly coupled to the second film layer at the opposing sides and along the length of the fluid distribution lumen. A delivery aperture may be disposed into the fluid distribution lumen and in fluid communication with the fluid distribution lumen. The fluid hub may be positioned in fluid communication with the fluid distribution lumen. The fluid hub may be positioned between the first film layer and the second film layer. Further, the fluid hub and the fluid distribution lumen may define a fluid instillation pathway.

In some embodiments, a method of manufacturing a treatment system for treating a tissue site may include defining a plurality of fluid distribution lumens between a first film layer and a second film layer, and disposing a delivery aperture into each of the plurality of fluid distribution lumens. The delivery aperture in each of the fluid distribution lumens may be in fluid communication therewith. The method may further include positioning a fluid hub in fluid communication with the fluid distribution lumens, forming a plurality of leg members, and positioning the plurality of leg members in fluid communication with a reduced-pressure hub.

In some embodiments, a method for providing fluid instillation and reduced pressure treatment at a tissue site may include positioning a dressing adjacent to the tissue site. The dressing may include a fluid instillation pathway and a reduced-pressure pathway separate from the fluid instillation pathway. The method may further include coupling a fluid instillation reservoir in fluid communication with the fluid instillation pathway, and coupling a reduced-pressure source in fluid communication with the reduced-pressure pathway. The coupling of the reduced-pressure source with the reduced-pressure pathway may be separate from the coupling of the fluid instillation source with the fluid instillation pathway. The method may further include supplying instillation fluid from the fluid instillation reservoir to the tissue site through the fluid instillation pathway. Additionally, the method may include providing reduced pressure from the reduced-pressure source to the tissue site through the reduced-pressure pathway, and extracting fluid from the tissue site through the reduced-pressure pathway.

Other aspects, features, and advantages of the illustrative embodiments will become apparent with reference to the drawings and detailed description that follow.

BRIEF DESCRIPTION OF THE DRAWINGS

FIG. 6 is an exploded, perspective view of a portion of another illustrative embodiment of a treatment system suitable for use with the dressing of FIG. 1;

DETAILED DESCRIPTION OF ILLUSTRATIVE EMBODIMENTS

In the following detailed description of non-limiting, illustrative embodiments, reference is made to the accompanying drawings that form a part hereof. Other embodiments may be utilized, and logical, structural, mechanical, electrical, and chemical changes may be made without departing from the scope of the appended claims. To avoid detail not necessary to enable those skilled in the art to practice the embodiments described herein, the description may omit certain information known to those skilled in the art. The following detailed description is non-limiting, and the scope of the illustrative embodiments are defined by the appended claims. As used herein, unless otherwise indicated, "or" does not require mutual exclusivity.

Figure 1:
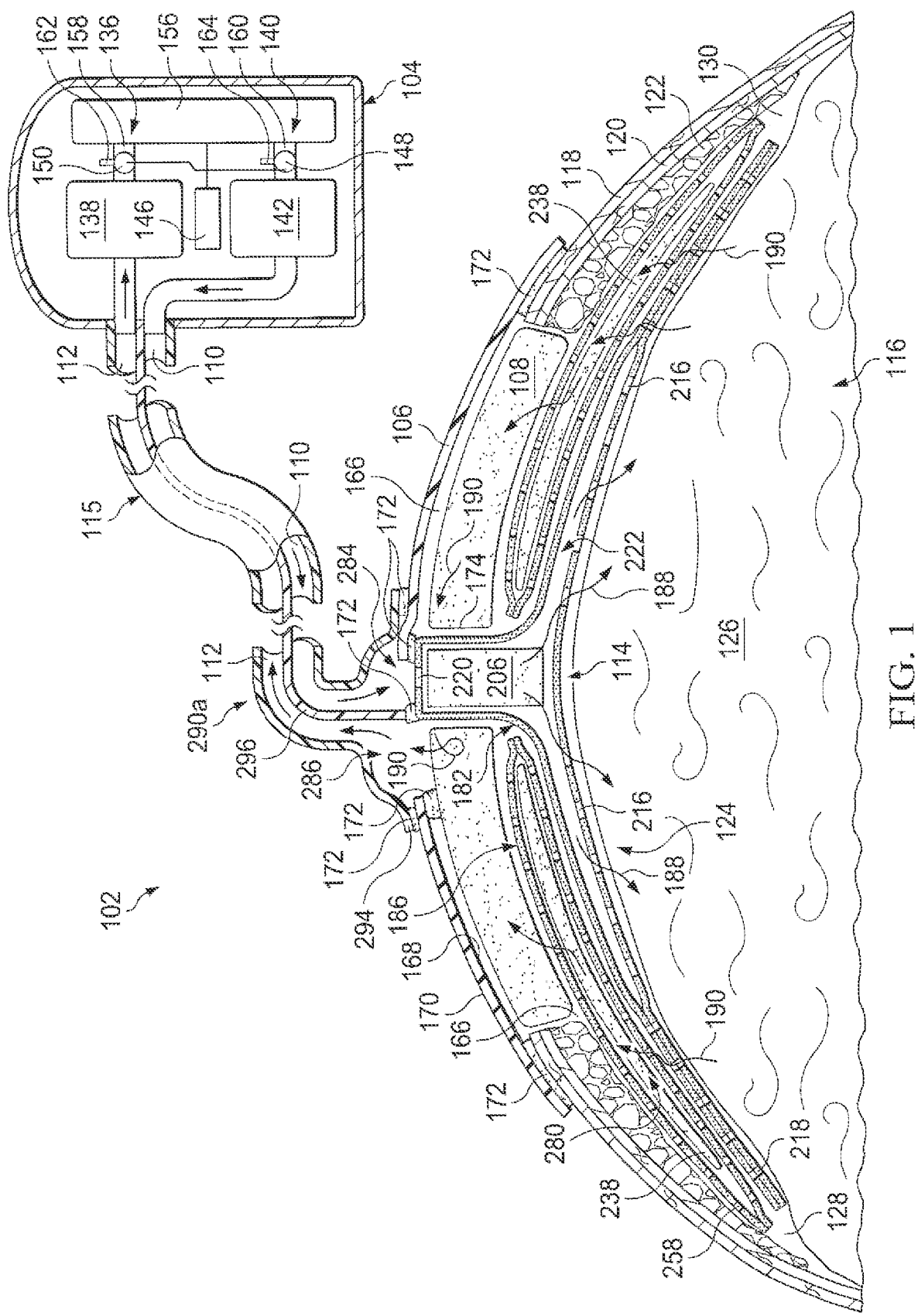
FIG. 1 is a cut-away view of an illustrative embodiment of a treatment system for providing fluid instillation and reduced pressure treatment at a tissue site, depicting an illustrative embodiment of a dressing for positioning at the tissue site.

Referring to FIG. 1, in some illustrative embodiments, a treatment system 102 may include a therapy device 104, a dressing sealing member 106, a distribution manifold 108, a fluid supply lumen 110, a reduced-pressure lumen 112, and a dressing 114. The treatment system 102 may be suitable for providing fluid instillation and reduced pressure treatment at a tissue site 116. The tissue site 116 may be may be the bodily tissue of any human, animal, or other organism, including bone tissue, adipose tissue, muscle tissue, dermal tissue, connective tissue, cartilage, tendons, ligaments, or any other tissue. The tissue site 116 may extend through or otherwise involve an epidermis 118, a dermis 120, and a subcutaneous tissue 122. The tissue site 116 may be a sub-surface tissue site as depicted in FIG. 1 that extends below the surface of the epidermis 118. Further, the tissue site 116 may be a surface tissue site (not shown) that predominantly resides on a surface of the epidermis 118.

As shown in FIG. 1, the tissue site 116 may include tissue in a body cavity such as, without limitation, an abdominal cavity 124. The abdominal cavity 124 may include abdominal contents 126 or other tissue proximate the abdominal cavity 124. The dressing 114 may be disposed in the abdominal cavity 124 and supported on a surface of the abdominal contents 126. The dressing 114 may also be positioned in or proximate to a left lateral or first paracolic gutter 128 and a right lateral or second paracolic gutter 130. The first paracolic gutter 128 and the second paracolic gutter 130 may each be, for example, an open space on opposing sides of the abdominal cavity 124 among the abdominal contents 126. The first paracolic gutter 128 may be laterally disposed from the second paracolic gutter 130 or otherwise positioned on an opposite side of the tissue site 116 from the second paracolic gutter 130. Although FIG. 1 depicts the treatment system 102 deployed at the abdominal cavity 124, the treatment system 102 may be used without limitation at other types of tissue sites. Further, the treatment of the tissue site 116 may include, without limitation, the removal of fluids, such as ascites and exudates, reduced-pressure therapy, instillation or distribution of fluids to the tissue site 116, and protection of the tissue site 116.

Continuing with FIG. 1, the therapy device 104 may be for coupling in fluid communication with the fluid supply lumen 110 and the reduced-pressure lumen 112. The fluid supply lumen 110 and the reduced-pressure lumen 112 may be coupled in fluid communication with the dressing 114 as described below. Further, the fluid supply lumen 110 and the reduced-pressure lumen 112 may be combined or formed as part of a multi-lumen conduit 115 as shown in FIG. 1. Referring to another illustrative embodiment in FIG. 6, the fluid supply lumen 110 and the reduced-pressure lumen 112 may be separate conduits, tubes, or pipes, for example.

The therapy device 104 may include a reduced-pressure source 136, a canister 138, a positive-pressure source 140, and a fluid instillation reservoir 142. The canister 138 and the fluid instillation reservoir 142 may each be any suitable containment device for holding a liquid and communicating fluids. Further, in some embodiments, the therapy device 104 may include a controller 146, a positive-pressure valve 148, and a reduced-pressure valve 150 for controlling components of the therapy device 104 as described below. The components of the therapy device 104 may be arranged or associated with one another as shown in FIG. 1 to form the therapy device 104. However, in other embodiments (not shown), the components of the therapy device 104 may be provided separately or independently from the therapy device 104.

The reduced-pressure source 136 may be for coupling in fluid communication with the reduced-pressure lumen 112. The canister 138 may be positioned in fluid communication with the reduced-pressure source 136. The reduced-pressure source 136 may be adapted to be coupled in fluid communication with the reduced-pressure lumen 112 through the canister 138. Thus, the canister 138 may have an inlet for receiving reduced pressure from the reduced-pressure source 136 and an outlet for delivering the reduced pressure to the reduced-pressure lumen 112. The reduced-pressure source 136, the reduced-pressure lumen 112, and the canister 136 may be fluidly coupled to one another in any suitable manner, such as, without limitation, through tubing, piping, adhesives, bonding, welding, couplers, or interference fit.

The positive-pressure source 140 may be for coupling in fluid communication with the fluid supply lumen 110. The fluid instillation reservoir 142 may be positioned in fluid communication with the positive-pressure source 140. The positive-pressure source 140 may be adapted to be coupled in fluid communication with the fluid supply lumen 110 through the fluid instillation reservoir 142. Thus, the fluid instillation reservoir 142 may have an inlet for receiving positive pressure from the positive-pressure source 140 and an outlet for delivering the positive pressure and instillation fluid to the fluid supply lumen 110. Instillation fluid may be urged from the fluid instillation reservoir 142 by the positive pressure into the fluid supply lumen 110. The positive-pressure source 140, the fluid supply lumen 110, and the fluid instillation reservoir 142 may be fluidly coupled to one another in any suitable manner, such as, without limitation, through tubing, piping, adhesives, bonding, welding, couplers, unions, or interference fit.

As shown in FIG. 1, a portable pump 156 may provide both the reduced-pressure source 136 and the positive-pressure source 140. For example, the pump 156 may include a suction port or pump inlet 158 and an exhaust port or pump outlet 160. The pump inlet 158 may provide the reduced-pressure source 136, and the pump outlet 160 may provide the positive-pressure source 140. The reduced-pressure valve 150 may be positioned in fluid communication between the reduced-pressure lumen 112 and the pump inlet 158. Reduced pressure from the reduced-pressure source 136 may be communicated to the reduced-pressure lumen 112 through the pump inlet 158 and the reduced-pressure valve 150. The positive-pressure valve 148 may be positioned in fluid communication between the fluid supply lumen 110 and the pump outlet 160. Positive pressure from the positive-pressure source 140 may be communicated to the fluid supply lumen 110 through the pump outlet 160 and the positive-pressure valve 148. Positive pressure applied to the dressing 114 may assist with communicating and distributing instillation fluid from the fluid instillation reservoir 142 to the dressing 114 and the tissue site 116. Fluid head, gravitational forces, and other factors may assist with communicating and distributing instillation fluid to the dressing 114 and the tissue site 116 with or without the application of positive pressure. Thus, some embodiments may not require the positive-pressure source 140.

In other embodiments, one pump or a first pump may provide the reduced-pressure source 136 and another pump or a second pump (not shown) may provide the positive-pressure source 140. Further, in other embodiments, the reduced-pressure source 136 may be any suitable device for providing reduced pressure, such as, for example, a wall suction source, a hand pump, or other source. Similarly, in other embodiments, the positive-pressure source 140 may be any suitable device for providing positive pressure, such as, for example, a compressor, compressed air cylinder, peristaltic pump, or similar source.

The reduced-pressure source 136 and the positive-pressure source 140 may be configured to supply reduced pressure and positive pressure, respectively, to the dressing 114 and the tissue site 116 in any combination or manner suitable for a particular application. For example, the controller 146 may be electrically coupled in any suitable manner to the reduced-pressure valve 150, the positive-pressure valve 148, and the pump 156. The controller 146 may include software or user programmable settings for controlling the reduced-pressure valve 150, the positive-pressure valve 148, and the pump 156 in relation to one another. In embodiments using a first pump for the reduced-pressure source 136 and a second pump for the positive-pressure source 140, the first pump and the second pump may be controlled by the controller 146 analogous to the reduced-pressure valve 150 and the positive-pressure valve 148 as described herein. In other embodiments, the reduced-pressure valve 150 and the positive-pressure valve 148 may be opened and closed or otherwise controlled manually by a user. Similarly, the pump 156 may be manually controlled.

In some embodiments, the pump 156 may be activated and the reduced-pressure valve 150 may be opened or otherwise activated simultaneously with the positive-pressure valve 148 for communicating reduced pressure and positive pressure to the tissue site 116 at the same time. The activation of the reduced-pressure valve 150 for reduced pressure delivery and the positive-pressure valve 148 for positive pressure delivery may be intermittent or continuous. In other embodiments, the pump 156 may activated and the reduced-pressure valve 150 may be configured to operate cyclically in relation to the positive-pressure valve 148. For example, the reduced-pressure valve 150 may be opened or activated to communicate reduced pressure to the dressing 114 and the tissue site 116 during a reduced-pressure therapy cycle. During the reduced-pressure therapy cycle, the positive-pressure valve 148 may be closed or inactive. During an instillation fluid cycle, the positive-pressure valve 148 may be opened or activated to communicate positive pressure to the dressing 114 and the tissue site 116. The reduced-pressure valve 150 may be closed or inactive during the instillation fluid cycle. The reduced-pressure valve 150 may have a reduced-pressure vent 162 for venting reduced pressure to the atmosphere, for example, when the reduced-pressure valve 150 is closed or inactive during the instillation fluid cycle. Similarly, the positive-pressure valve 148 may have a positive-pressure vent 164 for venting positive pressure to the atmosphere, for example, when the positive-pressure valve 148 is closed or inactive during the reduced-pressure therapy cycle.

Reduced pressure may be applied to the tissue site 116 from the reduced-pressure source 136 to promote removal of ascites, exudates, or other fluids from the tissue site 116. The fluid removed from the tissue site 116 by operation of reduced pressure being applied to the tissue site 116 may be about 5 liters or more per day. Further, reduced pressure may be applied to stimulate the growth of additional tissue, and to enhance the distribution of instillation fluids to the tissue site 116, if applicable. In the case of a wound at the tissue site 116, the growth of granulation tissue, removal of exudates, or removal of bacteria may promote healing. In the situation of a non-wounded or non-defective tissue, reduced pressure may promote the growth of tissue that may be harvested and transplanted to another tissue site.

As used herein, "reduced pressure" may refer to a pressure less than the ambient pressure at a tissue site being subjected to treatment. In some embodiments, the reduced pressure may be less than the atmospheric pressure. The reduced pressure may also be less than a hydrostatic pressure at a tissue site. Unless otherwise indicated, values of pressure stated herein are gauge pressures. The reduced pressure delivered may be a constant pressure, varied pressure, intermittent pressure, or continuous pressure. Although the terms "vacuum" and "negative pressure" may be used to describe the pressure applied to a tissue site, the actual pressure applied to the tissue site may be more than the pressure normally associated with a complete vacuum. An increase in reduced pressure may correspond to a reduction in pressure (more negative relative to ambient pressure) and a decrease in reduced pressure may correspond to an increase in pressure (less negative relative to ambient pressure). While the amount and nature of reduced pressure applied to a tissue site may vary according to the application, in some embodiments, the reduced pressure may be between about −5 mm Hg to about −500 mm Hg. In other embodiments, the reduced pressure may be between about −100 mm Hg to about −200 mm Hg. In yet other embodiments, the reduced pressure may be between about −50 mm Hg to about −300 mm Hg.

Further, in some embodiments, components of the treatment system 102, such as, without limitation, the reduced-pressure source 136, the therapy device 104, or the controller 146, may include preset selectors for −100 mm Hg, −125 mm Hg, and −150 mm Hg of reduced pressure. Further, the treatment system 102 may also include a number of alarms, such as, for example, a blockage alarm, a leakage alarm, or a battery-low alarm.

The dressing sealing member 106 may be adapted to cover the dressing 114 and the tissue site 116 and to provide a fluid seal and a sealed space 166 between the dressing sealing member 106 and the tissue site 116. A portion of the dressing sealing member 106 may overlap tissue surrounding the tissue site 116, such as the epidermis 118. The dressing 114 and the distribution manifold 108 may be sized or otherwise adapted to be positioned in the sealed space 166. For example, the dressing sealing member 106 may include an interior facing side 168 and an exterior facing side 170 positioned opposite the interior facing side 168. The sealed space 166 may be provided between the interior facing side 168 of the dressing sealing member 106 and the tissue site 114. In some embodiments, the dressing sealing member 106 may comprise a liquid impermeable material adapted to cover the tissue site 116 and tissue surrounding the tissue site 116.

The dressing sealing member 106 may be formed from any material that may allow for a fluid seal. A fluid seal may be a seal adequate to maintain reduced pressure, if applicable, at a desired site. The dressing sealing member 106 may comprise, for example, one or more of the following materials: hydrophilic polyurethane; cellulosics; hydrophilic polyamides; polyvinyl alcohol; polyvinyl pyrrolidone; hydrophilic acrylics; hydrophilic silicone elastomers; an INSPIRE 2301 material from Expopack Advanced Coatings of Wrexham, United Kingdom having, for example, a moisture vapor transmission rate or MVTR (inverted cup technique) of 14400 g/m2/24 hours and a thickness of about 30 microns; a thin, uncoated polymer drape; natural rubbers; polyisoprene; styrene butadiene rubber; chloroprene rubber; polybutadiene; nitrile rubber; butyl rubber; ethylene propylene rubber; ethylene propylene diene monomer; chlorosulfonated polyethylene; polysulfide rubber; polyurethane (PU); EVA film; co-polyester; silicones; a silicone drape; a 3M Tegaderm® drape; a polyurethane (PU) drape such as one available from Avery Dennison Corporation of Pasadena, Calif.; polyether block polyamide copolymer (PEBAX), for example, from Arkema, France; Expopack 2327; or other appropriate material.

The dressing sealing member 106 may be vapor permeable and liquid impermeable, thereby allowing vapor and inhibiting liquids from exiting the sealed space 166. In some embodiments, the dressing sealing member 106 may be a flexible, breathable film, membrane, or sheet having a high MVTR of, for example, at least about 300 g/m2 per 24 hours. The use of a high MVTR material for the dressing sealing member 106 may permit moisture vapor to pass through the dressing sealing member 106, external to the sealed space 166, while maintaining the fluid seal described above. In other embodiments, a low or no vapor transfer drape might be used. In some embodiments, the dressing sealing member 106 may comprise a range of medically suitable films having a thickness between about 15 microns (μm) to about 50 microns (μm).

In some embodiments, an attachment device or interface adhesive 172 may be adapted to be positioned between the dressing sealing member 106 and the tissue site 116. For example, the interface adhesive 172 may be positioned on or applied to the interior facing side 168 of the dressing sealing member 106 for facing the tissue site 116. In some embodiments, the dressing sealing member 106 may be sealed directly against tissue surrounding the tissue site 116, such as the epidermis 118, by the interface adhesive 172. In other embodiments, the interface adhesive 172 may seal the dressing sealing member 106 against a gasket or drape (not shown) adapted to be positioned between the interface adhesive 172 and the epidermis 118.

The interface adhesive 172 may be a medically-acceptable adhesive and may take numerous forms, such as an adhesive sealing tape, drape tape, paste, hydrocolloid, hydrogel, or other suitable sealing device. The interface adhesive 172 may also be flowable. Further, the interface adhesive 172 may comprise, without limitation, an acrylic adhesive, rubber adhesive, high-tack silicone adhesive, polyurethane, or other adhesive substance. In some embodiments, the interface adhesive 172 may be a pressure-sensitive adhesive comprising an acrylic adhesive with coat weight, for example, of about 15 grams/m2 (gsm) to about 70 grams/m2 (gsm). The pressure-sensitive adhesive may be applied on a side of the dressing sealing member 106 adapted to face the epidermis 118 and the tissue site 116, such as the interior facing side 168 of the dressing sealing member 106. In some embodiments, the interface adhesive 172 may be a layer or coating applied to or positionable on the interior facing side 168 of the dressing sealing member 106. In some embodiments, the interface adhesive 172 may be continuous or discontinuous.

The distribution manifold 108 may be for positioning between the dressing sealing member 106 and the dressing 114. The distribution manifold 108 may be adapted to be positioned proximate to, adjacent to, or in direct contact with the dressing 114 at the tissue site 116, such as, for example, by cutting or otherwise shaping the distribution manifold 108 in any suitable manner to fit the tissue site 116 and the sealed space 166. In some embodiments, the distribution manifold 108 may be positioned proximate to, adjacent to, or in direct contact with a portion of the tissue site 116. The distribution manifold 108 may have a distribution manifold opening 174 disposed through the distribution manifold 108 and adapted to receive a portion of the dressing 114, for example, for coupling the dressing 114 in direct fluid communication with the fluid supply lumen 110. Further, the distribution manifold 108 may be adapted to be in fluid communication with the dressing 114 and the tissue site 116 for distributing reduced pressure to the dressing 114 and the tissue site 116.

The distribution manifold 108 may be formed from any manifold material or flexible bolster material that provides a vacuum space, or treatment space, such as, for example, a porous and permeable foam or foam-like material, a member formed with pathways, a graft, or a gauze. In some embodiments, any material or combination of materials may be used as a manifold material for the distribution manifold 108 provided that the manifold material is operable to distribute or collect fluid. For example, the term manifold may refer to a substance or structure capable of delivering fluids to or removing fluids from a tissue site through a plurality of pores, pathways, or flow channels. The plurality of pores, pathways, or flow channels may be interconnected to improve distribution of fluids provided to and removed from an area around the manifold. Examples of such manifolds may include, without limitation, devices that have structural elements arranged to form flow channels, cellular foam, such as open-cell foam, porous tissue collections, and liquids, gels, and foams that include or cure to include flow channels. Further, the distribution manifold 108 may be biocompatible. In some embodiments, the distribution manifold 108 may comprise a porous, hydrophobic material. In such an embodiment, the hydrophobic characteristics of the distribution manifold 108 may prevent the distribution manifold 108 from directly absorbing fluid, but may allow the fluid to pass through.

In some embodiments, the distribution manifold 108 may be a reticulated, open-cell polyurethane or polyether foam that is fluid permeable. One such material may be the VAC® GranuFoam® material available from Kinetic Concepts, Inc. of San Antonio, Tex. However, a material with a higher or lower density than GranuFoam® material may be desirable for the distribution manifold 108 depending on the application. Among the many possible materials, the following may be used without limitation: GranuFoam® material, Foamex® technical foam (www.foamex.com), a molded bed of nails structure, a patterned grid material such as those manufactured by Sercol Industrial Fabrics, 3D textiles such as those manufactured by Baltex of Derby, U.K., a gauze, a flexible channel-containing member, and a graft.

In other embodiments, the distribution manifold 108 may comprise a material including closed cells. The closed cells may not be fluidly connected to adjacent cells in the distribution manifold 108. The closed cells may be selectively disposed in the distribution manifold 108 to, for example, prevent transmission of fluids through perimeter surfaces of the distribution manifold 108. Other layers may be included in or on the distribution manifold 108, such as absorptive materials, wicking materials, hydrophobic materials, and hydrophilic materials. In some embodiments, the distribution manifold 108 may be enhanced with ionic silver and anti-microbial agents.

The dressing 114 may include an instillation assembly 182 and a reduced-pressure assembly 186 that may be coupled to the instillation assembly 182. The instillation assembly 182 may permit various fluids, such as, without limitation, medicines, irrigation fluids, instillation fluids, or therapeutic fluids, to be delivered to the tissue site 116 as shown by delivery arrows 188. After being delivered to the tissue site 114, these fluids and other fluids may be removed or extracted from the tissue site 114 by the reduced-pressure assembly 186 as shown by extraction arrows 190.

Figure 2:
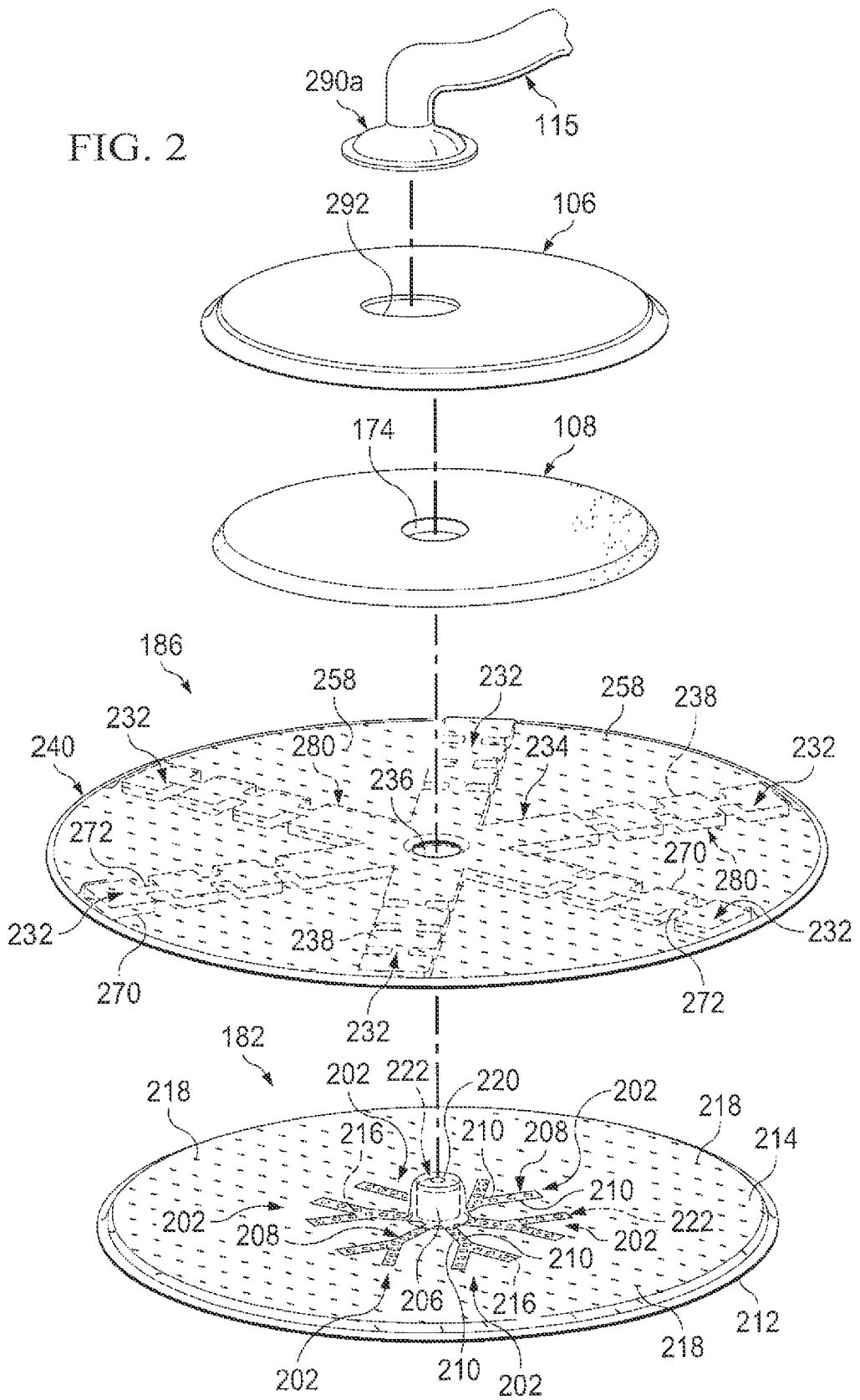
FIG. 2 is an exploded, perspective view of a portion of the treatment system and the dressing of FIG. 1, depicting an illustrative embodiment of an instillation assembly and a reduced-pressure assembly.

Referring to FIG. 2, the instillation assembly 182 may include at least one fluid distribution lumen 202 and a fluid hub 206. In some embodiments, the at least one fluid distribution lumen 202 may be a plurality of fluid distribution lumens 202 as shown in FIG. 2. In other embodiments, the instillation assembly 182 may include any number of the fluid distribution lumens 202, without limitation, to suit a particular application. The fluid distribution lumens 202 may be sized or otherwise adapted to be positioned in the sealed space 166 at the tissue site 116.

Each of the fluid distribution lumens 202 may have a length or branch 208 extending lengthwise and opposing sides 210 that may be positioned substantially normal to the length or the branch 208. The fluid distribution lumens 202 may be defined between or by a first film layer 212 and a second film layer 214. The first film layer 212 may be sealingly coupled to the second film layer 214 at the opposing sides 210 and along the length or the branch 208 of the fluid distribution lumens 202 in any suitable manner, such as, without limitation, welding, bonding, adhesives, cements, or similar bonding devices. The first film layer 212 may be adapted to be positioned between the second film layer 214 and the tissue site 116.

Further, each of the fluid distribution lumens 202 may include at least one delivery aperture 216 in fluid communication with the fluid distribution lumen 202 carrying the delivery aperture 216. In some embodiments, the at least one delivery aperture 216 may be a plurality of delivery apertures 216 as shown in FIG. 2. The fluid distribution lumens 202 may include any number of the delivery apertures 216, without limitation, to suit a particular application. Further, the delivery apertures 216 may be sized, shaped, or positioned in a configuration for delivering fluids to the tissue site 116 in a substantially even manner. The delivery apertures 216 may be disposed through the first film layer 212 into the fluid distribution lumen 202, and the first film layer 212 may be adapted to face the tissue site 116.

The first film layer 212 and the second film layer 214 may comprise a non-adherent material, such as a medical drape, capable of inhibiting tissue from adhering to the medical drape. In some embodiments, the first film layer 212 and the second film layer 214 may comprise a breathable polyurethane film. Further, in some embodiments, the first film layer 212 and the second film layer 214 may comprise any of the materials recited above for the dressing sealing member 106. Even further, in some embodiments, at least a portion of the first film layer 212 may be hydrophilic. For example, the first film layer 212 may comprise a plasma treatment that may impart hydrophilic properties to the first film layer 212. Such hydrophilic properties may encourage or improve fluid coverage over a greater surface of the first film layer 212 rather than, for example, being drawn to a low point at the tissue site 116 by operation of gravitational forces.

In some embodiments, the first film layer 212 and the second film layer 214 may include a plurality of openings or film fenestrations 218. The film fenestrations 218 may take a variety of shapes, such as, without limitation, circular openings, rectangular openings, polygon-shaped openings, slits, or linear cuts. Further, the film fenestrations 218 may have a variety of sizes to suit a particular application for providing a desired fluid flow, pressure delivery, or other parameters. The film fenestrations 218 may provide or enhance fluid communication between and among the tissue site 116, the reduced-pressure assembly 186, and the distribution manifold 108. The fluid delivery lumens 202 and the fluid delivery hub 206 may be free of the film fenestrations 218.

Further, in other embodiments, the instillation assembly 182 may be free of the film fenestrations 218. In such an embodiment, a surface area of the instillation assembly 182 may be reduced in size relative to the reduced-pressure assembly 186, for example, by decreasing a circumference, perimeter, or diameter of the instillation assembly 182. Reducing the surface area of the instillation assembly 182 may permit a periphery of the reduced-pressure assembly 186 to extend beyond a periphery of the instillation assembly 182 for positioning the reduced-pressure assembly 186 in direct fluid communication or contact with the tissue site 116.

The fluid hub 206 may have a height and may be positioned in fluid communication with the fluid distribution lumens 202. The height of the fluid hub 206 may extend outward from a surface of the second film layer 214 and the instillation assembly 182. The fluid hub 206 may be positioned between the first film layer 212 and the second film layer 214. A fluid hub port 220 may be disposed through the second film layer 214, and may provide fluid communication between the fluid supply lumen 110 and the fluid hub 206. The fluid distribution lumens 202 may be positioned circumferentially and substantially symmetric about the fluid hub 206. The fluid hub 206 and the fluid distribution lumens 202 may define a fluid instillation pathway 222. The instillation assembly 182 may be positioned between the tissue site 116 and the reduced-pressure assembly 186. As shown in FIG. 2, the fluid distribution lumens 202 may extend outward from the fluid hub 206 and across an oval or circular area having a maximum lengthwise dimension between about 260 millimeters to about 300 millimeters. In other embodiments, the fluid distribution lumens 202 may extend across an area having any desired dimensions and shape, for example, circular, oval, square, rectangular, or other.

As shown in FIG. 2, the fluid hub 206 may comprise a porous or fluid permeable material, such as, for example, a foam. Further, the fluid hub 206 may be elongate and cylindrical in shape. However, the fluid hub 206 may have other shapes without limitation. In other embodiments, the fluid hub 206 may comprise a fitting, such as a tube, tubular fitting, pipe, barbed connection, or similar structure. In such embodiments, the fitting may be pre-bonded or molded directly to the first film layer 212 or the second film layer 214 and configured to be fluidly coupled between the fluid supply lumen 110 and the fluid distribution lumens 202.

The fluid instillation pathway 222 may be adapted to deliver fluids to the tissue site 116 in a substantially uniform manner. For example, each of the fluid distribution lumens 202 and the delivery apertures 216 on the fluid instillation pathway 222 may be adapted to provide substantially the same back-pressure. Such a configuration may prevent fluid from traveling more freely through or otherwise favoring one of the fluid distribution lumens 202 over another of the fluid distribution lumens 202, or one of the delivery apertures 216 over another of the delivery apertures 216. Herein, back-pressure may refer a resistance to fluid flow, such as through the confined space of a lumen or aperture. Back-pressure may result from the geometric configuration and material properties of the confined space, such as, without limitation, the size of the space, the presence and shape of bends or joints in the space, surface finishes within the space, and other characteristics.

Fluids may tend to follow a path of least resistance, and thus, poor fluid distribution may result from one of the fluid distribution lumens 202 having less back-pressure or resistance to fluid flow than another of the fluid distribution lumens 202. Similarly, poor fluid distribution may result from one of the fluid delivery apertures 216 having less back-pressure or resistance to fluid flow than another of the fluid delivery apertures 216. Consistency among the size and configuration of the fluid distribution lumens 202, and the number and size of the delivery apertures 216 in each of the fluid distribution lumens 202, for example, may enhance the uniformity of fluid delivery to the tissue site 116. Thus, in some embodiments, the delivery apertures 216 may be substantially equal in number and size on each of the fluid distribution lumens 202. Further, each of the fluid distribution lumens 202 may have substantially the same dimensions.

For example, in some embodiments, the fluid distribution lumens 202 may have an internal diameter between about 2 millimeters to about 6 millimeters. Further, in some embodiments, the fluid distribution lumens 202 may have an internal diameter of about 4 millimeters. The delivery apertures 216, in some embodiments, may have a diameter between about 0.1 millimeters to about 0.8 millimeters. Sizing the internal diameter or cross-section of the fluid distribution lumens 202 substantially larger than the size, cross-section, or diameter of the fluid delivery apertures 216, as described herein, may provide a substantially uniform pressure within each of the fluid distribution lumens 202. In such an embodiment, fluid flow velocity within the distribution lumens 202 may be substantially low or substantially static relative to the high fluid flow velocity through the delivery apertures 216.

In some embodiments, each of the fluid distribution lumens 202 may have six (6) of the delivery apertures 216 disposed through the first film layer 212 in fluid communication with the fluid distribution lumen 202. Each of the six delivery apertures 216 may have a diameter of about 0.5 millimeters. In other embodiments, each of the fluid distribution lumens 202 may have twelve (12) of the delivery apertures 216 disposed through the first film layer 212 in fluid communication with the fluid distribution lumen 202. Each of the twelve (12) delivery apertures 216 may have a diameter of about 0.35 millimeters. Such configurations may provide sufficient back-pressure, for example, for a fluid instillation or delivery rate to the instillation assembly 182 that may be between about 80 cc/min to about 120 cc/min. Other configurations and fluid delivery rates are possible. In general, an increase in the number of the delivery apertures 216 may correspond to a decrease in the diameter of each of the delivery apertures 216 that may be required for maintaining a desired amount or range of back-pressure.

Continuing with FIG. 2, the reduced-pressure assembly 186 may include at least one leg member 232 and a reduced-pressure hub 234. In some embodiments, the at least one leg member 232 may be a plurality of leg members 232 as shown in FIG. 2. The reduced-pressure assembly 186 may include any number of the leg members 232 to suit a particular application without limitation. The leg members 232 may be sized or otherwise adapted to be positioned in the sealed space 166. Further, in some embodiments, the reduced-pressure assembly 186 may include a central opening 236 disposed through or at the reduced-pressure hub 234 and sized or otherwise adapted to receive the fluid hub 206. The height of the fluid hub 206 may be sized or otherwise adapted to extend through the central opening 236. In other embodiments, the central opening 236 may have any shape, size, or configuration suitable to provide access for direct physical coupling or direct fluid coupling of the fluid supply lumen 110 to the second film layer 214 and/or the fluid hub 206 of the instillation assembly 182.

Each of the leg members 232 may include a leg manifold 238 and a leg encapsulating material 240 that may cover the leg manifold 238 while permitting fluid communication with the leg manifold 238. In other embodiments, the leg manifold 238 or the leg encapsulating material 240 may be omitted. The leg manifold 238 may comprise a porous or fluid permeable material, such as, for example, a foam. In some embodiments, the leg manifold 238 may comprise any of the materials recited above for the distribution manifold 108. The leg encapsulating material 240 may cover the leg manifold 238 and may preclude tissue from adhering to the leg manifold 238 or otherwise coming into contact with the leg manifold 238. Precluding such contact between tissue and the leg manifold 238 may, for example, provide for a broader range of materials to be used for the leg manifold 238 and treatment applications for the dressing 114.

Figure 3:
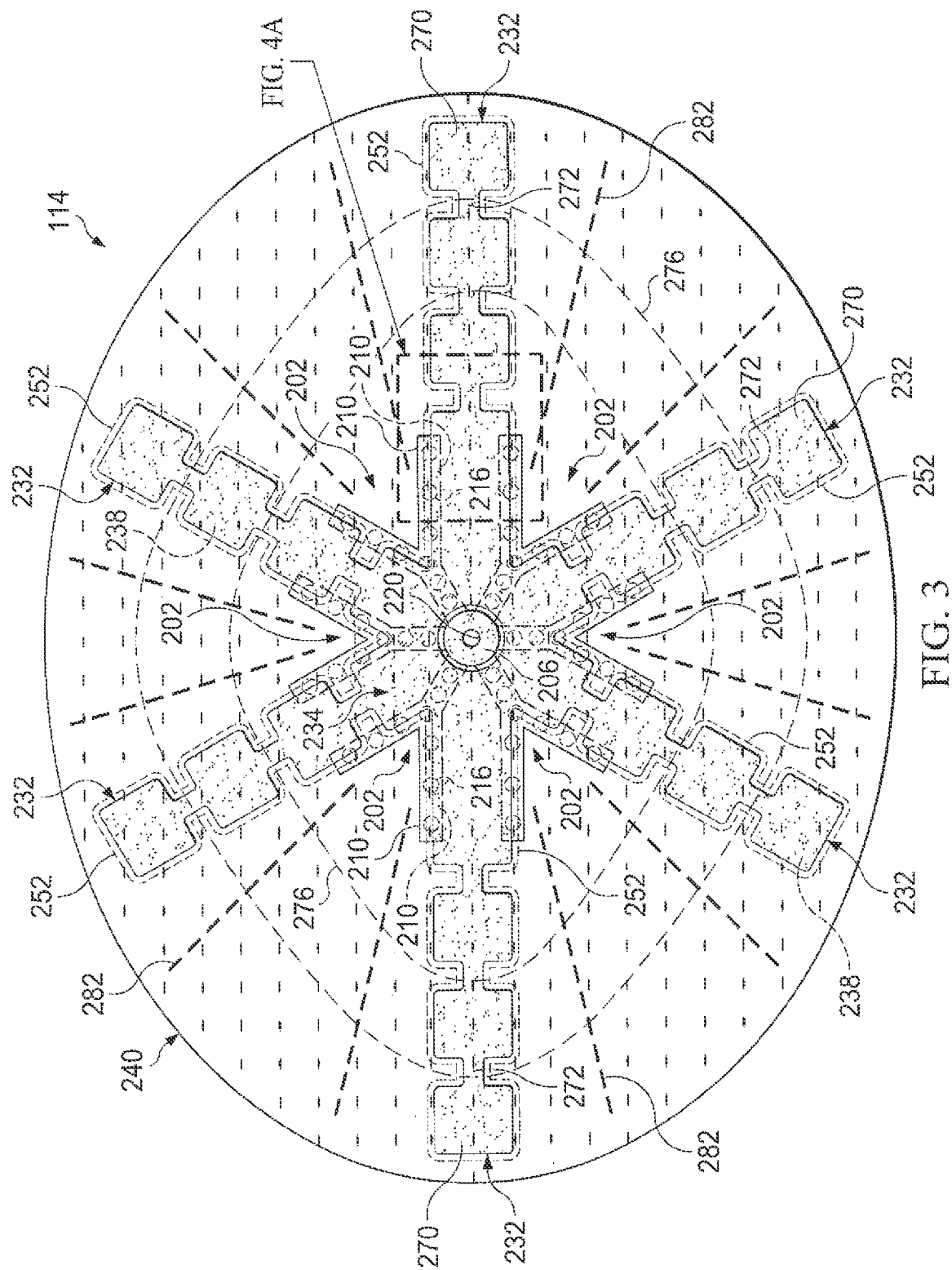
FIG. 3 is a top, plan view of the dressing of FIG. 1.
Figure 4A:
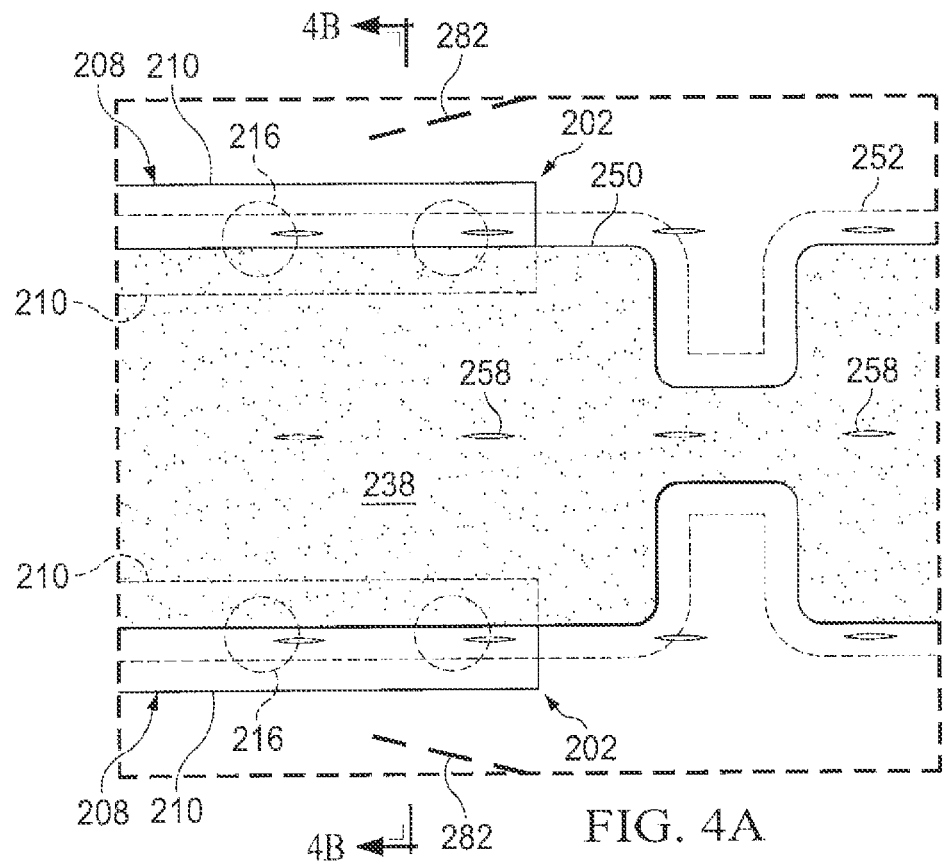
FIG. 4A is detail view of a portion of the dressing of FIG. 1 taken at reference FIG. 4A depicted in FIG. 3.
Figure 4B:
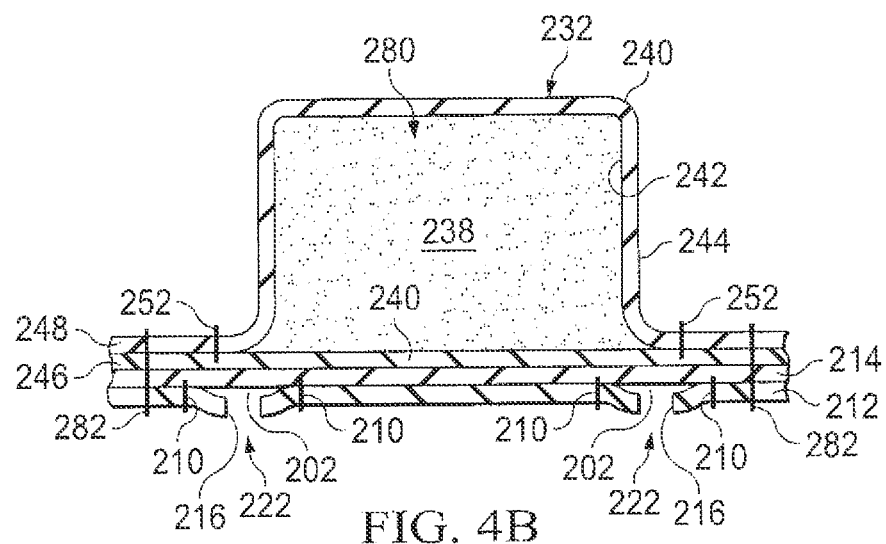
FIG. 4B is a cross section of the dressing of FIG. 1 taken at lines 4B-4B referenced in FIG. 4A.

Referring to FIGS. 2-5, and particularly to the detail view of FIGS. 4A-4B, the leg encapsulating material 240 may define an interior 242 and an exterior 244 of the leg member 232. The leg manifold 238 may be positioned within the interior 242 of the leg member 232, and may be encapsulated by the leg encapsulating material 240 in any suitable manner. For example, the leg encapsulating material 240 may include a first encapsulating layer 246 and a second encapsulating layer 248. The leg manifold 238 may be positioned between the first encapsulating layer 246 and the second encapsulating layer 248. The first encapsulating layer 246 may be coupled to the second encapsulating layer 248 around perimeter edges 250 of the leg manifold 238 by a leg bond 252, such as, without limitation, a weld, adhesive, cement, or similar bonding device. A length of the leg bond 252 may be discontinuous, and thus, may enhance fluid communication with the leg members 232 and the leg manifold 238 through the first encapsulating layer 246 and the second encapsulating layer 248.

Figure 5:
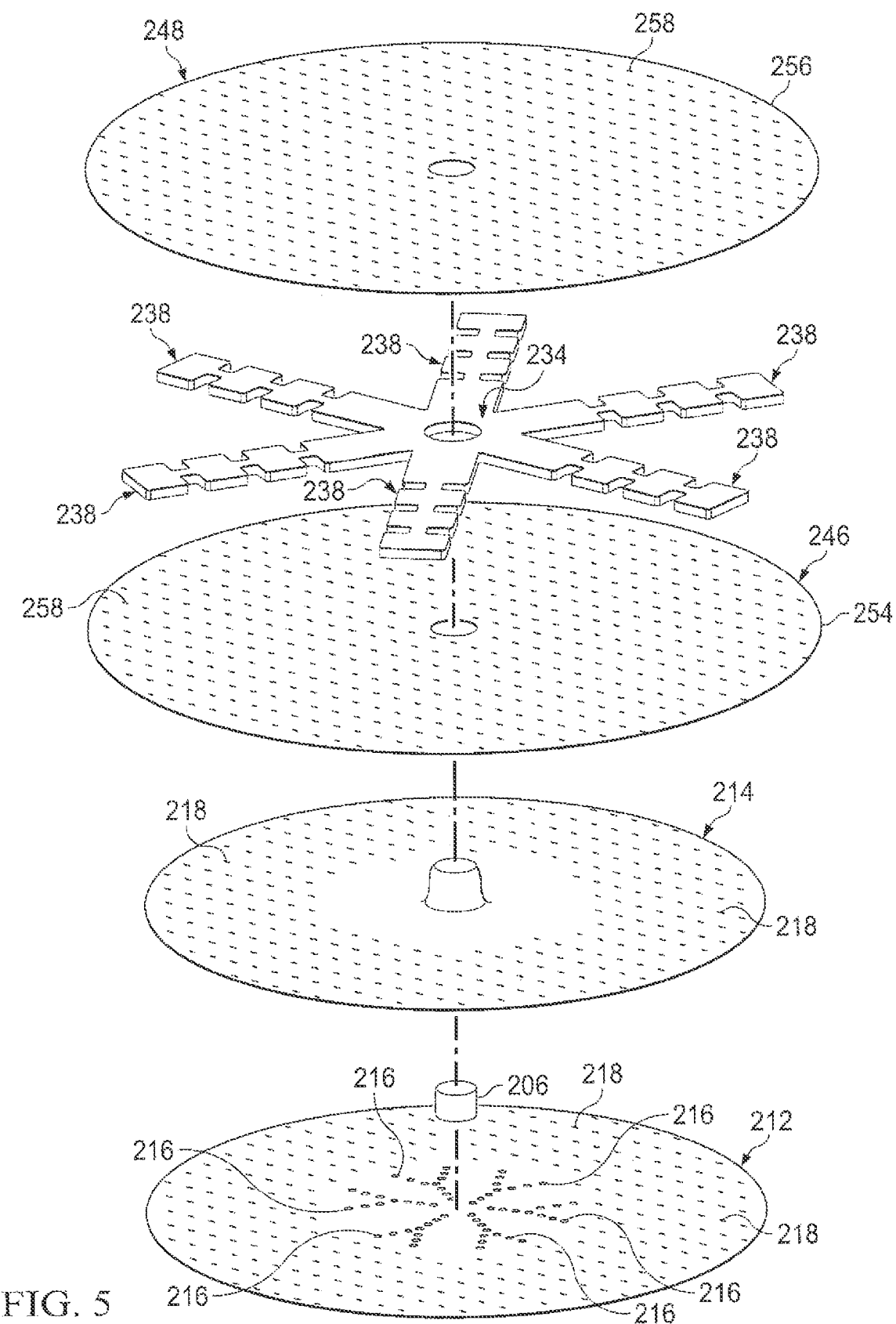
FIG. 5 is an exploded, perspective view of the illustrative embodiments of the instillation assembly and the reduced-pressure assembly of the dressing of FIG. 1.

Referring to FIG. 5, the first encapsulating layer 246 may have a first periphery 254 sized or otherwise adapted to mate with a second periphery 256 of the second encapsulating layer 248. The first periphery 254 may be coupled to the second periphery 256 in any suitable manner, such as, without limitation, by any of the bonding devices described above for the leg bond 252. In other embodiments, the leg encapsulating material 240 may be a single layer sized and shaped to wrap around or cover the leg manifold 238, or otherwise form the leg member 232. Further, in other embodiments, the leg encapsulating material 240 may be multiple layers coupled to one another around or covering the leg manifold 238, or otherwise forming the leg member 232.

Continuing with FIGS. 2-5, a plurality of leg fenestrations 258 may be disposed through the leg encapsulating material 240 in fluid communication between the leg manifold 238 and the exterior 244 of the leg member 232. The leg fenestrations 258 may take a variety of shapes, such as, without limitation, circular openings, rectangular openings, polygon-shaped openings, slits, or linear cuts. Further, the leg fenestrations 258 may have a variety of sizes to suit a particular application for providing a desired fluid flow, pressure delivery, or other parameters. The leg fenestrations 258 may provide or enhance fluid communication, without limitation, between and among the tissue site 116, the reduced-pressure assembly 186, the distribution manifold 108, and the reduced-pressure lumen 112.

The leg encapsulating material 240 may comprise a non-adherent material, such as a medical drape, capable of inhibiting tissue from adhering to the medical drape. In some embodiments, the leg encapsulating material 240 may comprise a breathable polyurethane film. Further, in some embodiments, the leg encapsulating material 240 may comprise any of the materials recited above for the dressing sealing member 106.

The leg members 232 may extend outward from the reduced-pressure hub 234 and be positioned in fluid communication with the reduced-pressure hub 234 in any suitable shape or configuration. As shown in FIGS. 2-3, the leg members 232 may extend radially outward from the reduced-pressure hub 234. The reduced-pressure hub 234 may be a region of the reduced-pressure assembly 186 where the leg members 232 are gathered, coupled, or otherwise directed toward one another. The region of the reduced-pressure assembly 186 providing the reduced-pressure hub 234 may, for example, be a center region of the reduced-pressure assembly 186.

As shown in FIGS. 2-3, in some embodiments, the leg members 232 may be coupled together, for example, with the leg encapsulating material 240 that may extend between each of the leg members 232. Further, in some embodiments, a portion of the leg encapsulating material 240 between the adjacent leg members 232 may be expandable, stretchable, flexible, elastic, or otherwise deformable for permitting movement among distal ends of the leg members 232. In other embodiments, the distal ends of the leg members 232 may be independently movable relative to one another while proximal ends of the leg members 232 may be coupled or gathered at the reduced-pressure hub 234.

The leg members 232 may take a number of different lengths and shapes, such as elongate shapes, rectangular, elliptical, and other shapes. As shown in FIGS. 2-5, in some embodiments, the leg members 232 may include a plurality of leg modules 270 positioned along the length of the leg members 232. A manipulation zone 272 may be positioned between each of the adjacent leg modules 270 along the length of the leg members 232. The manipulation zones 272 may provide regions having a reduced size relative to the leg modules 270 that may enhance separation or removal the leg modules 270 for sizing the dressing 114. In some embodiments, the manipulation zones 272 may include a weakened or perforated area to facilitate sizing of the dressing 114, for example, by cutting or tearing. The leg modules 270 on each of the leg members 232 may be in fluid communication with one another. In some embodiments, a clinician may cut through the manipulation zones 272, or tear through the manipulation zones 272 by pulling, to size the dressing 114. Further, as shown in FIG. 3, in some embodiments, visual indicia 276 may be applied on a surface of the dressing 114 or the leg members 232 as a guide for sizing the dressing 114. The visual indicia 276 may comprise, for example, cut lines or size graduations that may cross through the manipulation zones 272 to provide convenience in cutting, tearing, or otherwise sizing the dressing 114. In such embodiments, the fluid distribution lumens 202 may reside within or inbound of the visual indicia 276 indicating the smallest size possible for the dressing 114 to, for example, preclude severing the fluid distribution lumens 202 when sizing the dressing 114. In other embodiments, where sizing the dressing 114 may not be a feature or concern, for example, the fluid distribution lumens 202 may extend into or reside within any area of the dressing 114 as desired.

The reduced-pressure hub 234 and the leg members 232 may define a reduced-pressure pathway 280, shown, for example, in FIGS. 1, 2, and 4B, that is separate from the fluid instillation pathway 222. Fluid may flow from the leg members 232 towards the reduced-pressure hub 234. The fluid may enter the leg fenestrations 258 and flow into the leg members 232 and toward the reduced-pressure hub 234 as shown by the fluid extraction arrows 190 in FIG. 1. The first film layer 212 and the second film layer 214 of the instillation assembly 182 may separate the fluid distribution lumens 202 and the fluid hub 206 from the leg members 232 and the reduced-pressure hub 234 of the reduced-pressure assembly 186. The fluid distribution lumens 202 may be positioned between the tissue site 116 and the leg members 232. Further, the second film layer 214 may be positioned between the first film layer 212 and the reduced-pressure pathway 280.

As shown in FIGS. 3-4B, the reduced-pressure assembly 186 may be coupled to the instillation assembly 182 by an assembly bond 282 that may comprise, without limitation, any of the bonding devices described above in connection with the leg bond 252. Thus, the assembly bond 282 may couple the first film layer 212, the second film layer 214, the first encapsulating layer 246, and the second encapsulating layer 248 together.

The distribution manifold 108 may be adapted to be positioned adjacent to the reduced-pressure hub 234 of the reduced-pressure assembly 186 and between the dressing sealing member 106 and the leg members 232 of the reduced-pressure assembly 186. The distribution manifold 108 may be adapted to distribute reduced pressure to the leg members 232. In some embodiments, the distribution manifold 108 may be adapted to distribute reduced pressure to the leg members 232 through the reduced-pressure hub 234.

In some embodiments, the distribution manifold opening 174 disposed through the distribution manifold 108 may receive the fluid hub 206 of the instillation assembly 182. The height of the fluid hub 206 may be sized or otherwise adapted to extend through the distribution manifold opening 174.

The fluid supply lumen 110 may be for positioning in fluid communication with the instillation assembly 182. For example, the fluid supply lumen 110 may be adapted to be coupled in fluid communication with the fluid hub 206 at a fluid supply connection 284, shown in FIG. 1, that may be on or extending through the dressing sealing member 106.

The reduced-pressure lumen 112 may be for positioning in fluid communication with the reduced-pressure assembly 186. For example, the reduced-pressure lumen 112 may be adapted to be coupled in fluid communication with the reduced-pressure hub 234 at a reduced-pressure connection 286 that may be on or extending through the dressing sealing member 106, as shown in FIG. 1. In some embodiments, the reduced-pressure lumen 112 may be adapted to be coupled in fluid communication with the reduced-pressure hub 234 through the distribution manifold 108. The reduced-pressure lumen 112 may have a length between the reduced-pressure connection 286 and the reduced-pressure source 136 that is fluidly isolated from an entire length of the fluid supply lumen 110. The length of the fluid supply lumen 110 may be between the fluid supply connection 284 and the fluid instillation reservoir 142. Further, the reduced-pressure lumen 112 and the reduced-pressure connection 286 may be fluidly isolated from the fluid supply lumen 110 and the fluid supply connection 284.

Referring to FIGS. 1-2, a conduit interface 290 may provide the reduced-pressure connection 286 and the fluid supply connection 284. The conduit interface 290 may be sized, shaped, or otherwise adapted to fluidly connect the reduced-pressure lumen 112 and the fluid supply lumen 110 to the dressing 114 through the dressing sealing member 106 in any suitable manner. For example, one or more sealing member aperture 292 may be disposed through the dressing sealing member 106 to provide fluid communication and access to the distribution manifold 108, the dressing 114, and other components positioned in the sealed space 166. The sealing member aperture 292 may facilitate the fluid connection, without limitation, of the fluid supply lumen 110, the reduced-pressure lumen 112, and the conduit interface 290 with the distribution manifold 108 and the dressing 114. Further, portions of the dressing sealing member 106 proximate the sealing member aperture 292 may be coupled to the distribution manifold 108 and the dressing 114 with, for example, an adhesive, such as the interface adhesive 172, as necessary for fluidly isolating the reduced-pressure connection 286 from the fluid supply connection 284.

In some embodiments, the conduit interface 290 may be formed or molded as part of the reduced-pressure lumen 112 and the fluid supply lumen 110. In other embodiments, the reduced-pressure lumen 112 and the fluid supply lumen 110 may be, for example, bonded or secured by an interference fit to the conduit interface 290. A portion of the conduit interface 290, such as a flange 294, may be coupled to the dressing sealing member 106 for positioning the conduit interface 290 in fluid communication with the dressing 114 through the dressing sealing member 106. The conduit interface 290 may be coupled to the dressing sealing member 106 in any suitable manner, such as, for example, by an adhesive or other bonding device. In some embodiments, the adhesive for coupling the conduit interface 290 to the dressing sealing member 106 may be the interface adhesive 172 used for the dressing sealing member 106 described above.

In some embodiments, as shown in FIGS. 1-2, the conduit interface 290 may be a multi-port interface 290*a* providing both the reduced-pressure connection 286 and the fluid supply connection 284 as individual, fluidly isolated ports within the multi-port interface 290*a*. In such an embodiment, a dividing wall 296 within the multi-port interface 290*a* may be coupled to the fluid hub 206 and/or the second film layer 214 by an adhesive, such as the interface adhesive 172, for fluidly isolating the fluid supply connection 284 from the reduced-pressure connection 286. Other configurations for fluidly isolating the reduced-pressure connection 286 from the fluid supply connection 284 are possible.

In other embodiments, as shown in FIG. 6, the conduit interface 290 may be a single-port interface 290*b* that may provide either the reduced-pressure connection 286 or the fluid supply connection 284. Thus, a first single-port interface 290*b* may provide the fluid supply connection 284, and a second single-port interface 290*b* may provide the reduced-pressure connection 286. In other embodiments, the fluid supply lumen 110 may be fluidly coupled directly to the fluid hub 206, and the reduced-pressure lumen 112 may be fluidly coupled directly to the distribution manifold 108 through the dressing sealing member 106 without the conduit interface 290.

Referring generally to FIGS. 1-4B, in some illustrative embodiments of operation of the treatment system 102, the dressing 114 may be sized to fit the tissue site 116 and disposed at or within the tissue site 116, such as the abdominal cavity 124. If sizing the dressing 114 is necessary, excess portions of the dressing 114 may be removed, for example, by cutting or tearing through the dressing 114 proximate the visual indicia 276 for a desired size. In some embodiments, the dressing 114 may be cut or torn through the leg modules 270 outboard of the visual indicia 276 for a desired size. The cut or torn portion of the leg modules 270 remaining attached to the dressing 114 may include a portion of the leg manifold 238 and a portion of the leg encapsulating material 240. The remaining portion of the leg manifold 238 may be separated from the dressing 114 at the adjacent or inbound manipulation zone 272 and removed from within the leg encapsulating material 240. In this manner, a portion of the leg encapsulating material 240 may remain attached to the dressing 114 extending beyond an edge of the leg manifold 238 for preventing contact between the leg manifold 238 and the tissue site 116.

The dressing 114 may be positioned in contact with the abdominal contents 126, and the leg members 232 may be positioned in or proximate to the first paracolic gutter 128 and the second paracolic gutter 130. When deployed, the dressing 114 may cover all exposed viscera and may separate the viscera from contact with the walls of the abdominal cavity 126. The dressing 114 may be sized and shaped to permit such coverage.

When the dressing 114 is disposed at the tissue site 116, the installation assembly 182 may be positioned facing the tissue site 116 and between the tissue site 116 and the reduced-pressure assembly 186. The distribution manifold 108 may be positioned adjacent to or in contact with the dressing 114 at the tissue site 116. For example, the distribution manifold 108 may be positioned adjacent to or in contact with the reduced-pressure hub 234 of the dressing 114. Further, the distribution manifold opening 174 may be positioned to engage or receive the fluid hub 206 of the installation assembly 182. The height of the fluid hub 206 may extend through the thickness of the distribution manifold 108 for contacting, without limitation, the dressing sealing member 106, the conduit interface 290, or the fluid supply lumen 110 for making the fluid supply connection 284 as described herein.

The distribution manifold 108 and the dressing 114 may be covered at the tissue site 116 with the dressing sealing member 106 to provide the sealed space 166 with the distribution manifold 108 and the dressing 114 positioned within the sealed space 166. The dressing sealing member 106 may be positioned and fluidly sealed about the tissue site 116 with the interface adhesive 172 as described above. The sealing member apertures 292 may be cut or otherwise disposed through the dressing sealing member 106 as necessary, if not already provided on the dressing sealing member 106. The reduced-pressure connection 286 and the fluid supply connection 284 may be made, for example, with the conduit interface 290 or through direct coupling of the reduced-pressure lumen 112 to the distribution manifold 108 and the fluid supply lumen 110 to the installation assembly 182.

Activating the reduced-pressure source 136 may provide reduced pressure to the reduced-pressure assembly 186 through the reduced-pressure lumen 112 and the distribution manifold 108. The installation fluid reservoir 142 may provide installation fluid to the installation assembly 182 through the fluid supply lumen 110, for example, by activating the positive-pressure source 140 or by operation of gravitational forces acting on the installation fluid. Reduced pressure and installation fluid may be provided to the dressing 114 simultaneously, at the same time, or cyclically, at alternate times. Further, reduced pressure and installation fluid may be applied to the dressing 114 intermittently or continuously.

When the reduced-pressure source 136 is activated, the distribution manifold 108 may distribute the reduced pressure to reduced-pressure hub 234 and to the leg members 232 of the reduced-pressure pathway 280 through the reduced-pressure hub 234. As shown in FIG. 1 by the extraction arrows 190, fluid from the tissue site 116 may be drawn or extracted through the film fenestrations 218 in the installation assembly 182 and the leg fenestrations 258 in the reduced-pressure assembly 186, entering the leg members 232. Fluid in the leg members 232 may be communicated through the leg members 232 and into the reduced-pressure hub 234 and the distribution manifold 108 where the fluid may be drawn into the reduced-pressure lumen 112 and the canister 138.

When the positive-pressure source is activated or installation fluid is otherwise being delivered to the dressing 114, the installation fluid may pass into the fluid hub 206 of the installation fluid pathway 222 through fluid hub port 220 as shown by the delivery arrows 188 in FIG. 1. From the fluid hub 206, the installation fluid may be communicated to the tissue site 116 through the fluid distribution lumens 202 and the delivery apertures 216 in the fluid distribution lumens 202. The configuration of the fluid installation pathway 222 and the associated back-pressure as described above may facilitate delivery of the installation fluid to the tissue site 116 in a substantially uniform manner.

Fluid being instilled or delivered to the tissue site 116 through the fluid installation pathway 222 may remain physically and fluidly separate from the reduced-pressure pathway 280 until reaching or coming into direct contact with the tissue site 116. Once delivered to the tissue site 116, the installation fluid may become comingled with, for example, previously instilled fluids, wound fluid, tissue fluids, and other fluids that may be considered waste fluid. When reduced pressure is being applied to the dressing 114, tissue or wound fluids from the tissue site 116 and any installation fluid previously delivered to the tissue site 116 may be extracted through the separate reduced-pressure pathway 280. Fluid being extracted from the tissue site 116 through the reduced-pressure pathway 280 may remain physically and fluidly separate from the installation fluid pathway 222. Such separation between the reduced-pressure pathway 280 and the fluid installation pathway 222 may prevent fluids that may remain, for example, in the leg members 232, the reduced-pressure hub 234, and the distribution manifold 108, after or during extraction from the tissue site 116, from being forced back into the tissue site 116 during fluid installation.

Further, the separation of the reduced-pressure pathway 280 from the fluid installation pathway 222 may promote efficient use of installation fluid. For example, as described above, the distribution manifold 108, the reduced-pressure hub 234, and the leg manifold 238 may comprise a porous, fluid permeable material, such as a foam. This fluid permeable material may include fluid flow passageways that may remain open or fluid permeable while under reduced pressure for extracting fluid from the tissue site 116. Further, fluid extracted from the tissue site 116 may be stored within the reduced-pressure assembly 186 of the dressing 114 before being drawn into the reduced-pressure lumen 112. The capability to provide fluid storage and permeability while under reduced pressure may require the distribution manifold 108 and the reduced-pressure assembly 186 to have a higher volume or fluid capacity compared to the fluid installation pathway 222 that may be under positive pressure. Fluid being instilled or delivered to the tissue site 116 through the separate fluid installation pathway 222 may not be required to pass through portions of the treatment system 102, such as the distribution manifold 108 and the reduced-pressure assembly 186, that may be higher volume. Such a configuration may enhance the distribution and efficient use of the installation fluid.

Continuing generally with FIGS. 1-4B, further described are methods for providing fluid installation and reduced pressure treatment at a tissue site. In some embodiments, a method for providing fluid installation and reduced pressure treatment at a tissue site may include positioning the dressing 114 adjacent to the tissue site 116. The dressing 114 may include the fluid installation pathway 222 and the reduced-pressure pathway 280 separate from the fluid installation pathway 222. The method may further include coupling the fluid installation reservoir 142 in fluid communication with the fluid installation pathway 222, and coupling the reduced-pressure source 136 in fluid communication with the reduced-pressure pathway 280. The coupling of the reduced-pressure source 136 with the reduced-pressure pathway 280 may be separate from the coupling of the fluid installation source 142 with the fluid installation pathway 222. The method may further include supplying installation fluid from the fluid instillation reservoir 142 to the tissue site 116 through the fluid instillation pathway 222. Additionally, the method may include providing reduced pressure from the reduced-pressure source 136 to the tissue site 116 through the reduced-pressure pathway 280, and extracting fluid from the tissue site 116 through the reduced-pressure pathway 280.

In some embodiments, the tissue site 116 may be the abdominal cavity 124, and positioning the dressing 114 adjacent to the tissue site 116 may include placing at least a portion of the dressing 114 proximate a paracolic gutter in the abdominal cavity 124, such as the first and/or the second paracolic gutter 128, 130.

In some embodiments, the method may further include disposing the distribution manifold 108 proximate to the dressing 114. Further, in some embodiments, the method may include covering the dressing 114 with the dressing sealing member 106 to provide the sealed space 166 between the dressing sealing member 106 and the tissue site 116. The distribution manifold 108 may be positioned within the sealed space 166. Providing reduced pressure from the reduced-pressure source 136 to the tissue site 116 through the reduced-pressure pathway 280 may include distributing the reduced pressure to the reduced-pressure pathway 280 through distribution manifold 108.

In some embodiments, the method may include sizing the dressing 114 for placement at the tissue site 116. Sizing the dressing 114 may include cutting or tearing the dressing 114 proximate the visual indicia 276 for a desired size.

Referring to FIGS. 3-5, further described are methods for manufacturing a treatment system for treating a tissue site. In some embodiments, a method of manufacturing the treatment system 102 for treating the tissue site 116 may include defining the plurality of fluid distribution lumens 202 between the first film layer 212 and the second film layer 214, and disposing the delivery aperture 216 into each of the fluid distribution lumens 202. The delivery aperture 216 in each of the fluid distribution lumens 202 may be in fluid communication with the fluid distribution lumen 202 carrying the delivery aperture 216. The method may further include positioning the fluid hub 206 in fluid communication with the fluid distribution lumens 202, forming the plurality of leg members 232, and positioning the leg members 232 in fluid communication with the reduced-pressure hub 234.

In some embodiments, defining the plurality of fluid distribution lumens 202 between the first film layer 212 and the second film layer 214 may include coupling the first film layer 212 to the second film layer 214 along the opposing sides 210 and the length of each of the fluid distribution lumens 202. The first film layer 212 may be adapted to face the tissue site 116. In some embodiments, the delivery aperture 216 disposed in each of the fluid distribution lumens 202 may be a plurality of delivery apertures 216. Thus, the method may further include disposing the plurality of delivery apertures 216 into each of the fluid distribution lumens 202. At least one of the delivery apertures 216 may be disposed through the first film layer 212 into each of the fluid distribution lumens 202. In some embodiments, the delivery apertures 216 may be equal in number and size, and each of the fluid distribution lumens 202 may have substantially the same dimensions. Further, the fluid distribution lumens 202 may be positioned circumferentially and substantially symmetric about the fluid hub 206. In some embodiments, positioning the fluid hub 206 in fluid communication with the fluid distribution lumens 202 may include positioning the fluid hub 206 between the first film layer 212 and the second film layer 214 before defining the fluid distribution lumens 202 or coupling the first film layer 212 to the second film layer 214.

In some embodiments, for each of the leg members 232, forming the plurality of leg members 232 may include encapsulating the leg manifold 238 within the leg encapsulating material 240, and disposing the plurality of leg fenestrations 258 through the leg encapsulating material 240 in fluid communication with the leg manifold 238.

In some embodiments, the leg encapsulating material 240 may include the first encapsulating layer 246 and the second encapsulating layer 248, and the method may further include positioning the leg manifold 238 between the first encapsulating layer 246 and the second encapsulating layer 248, and coupling the first encapsulating layer 246 to the second encapsulating layer 248 around the leg manifold 238.

In some embodiments, the method may further include disposing the central opening 236 through the reduced-pressure hub 234. The central opening 236 may be sized to receive the fluid hub 206. Further, the method may include positioning the fluid hub 206 within the central opening 236. The fluid hub 206 may have a height configured to extend through the central opening 236.

In some embodiments, the method may include positioning the second film layer 214 between the first film layer 212 and the plurality of leg members 232. The fluid distribution lumens 202 may be adapted to be positioned between the tissue site 116 and the plurality of leg members 232.

The method may additionally include coupling the first film layer 212, the second film layer 214, the first encapsulating layer 246, and the second encapsulating layer 248 together by the assembly bond 282. In some embodiments, coupling the first film layer 212 to the second film layer 214 and forming the plurality of leg members 232 may occur before coupling the first film layer 212, the second film layer 214, the first encapsulating layer 248, and the second encapsulating layer 248 together.

Figure 7A:
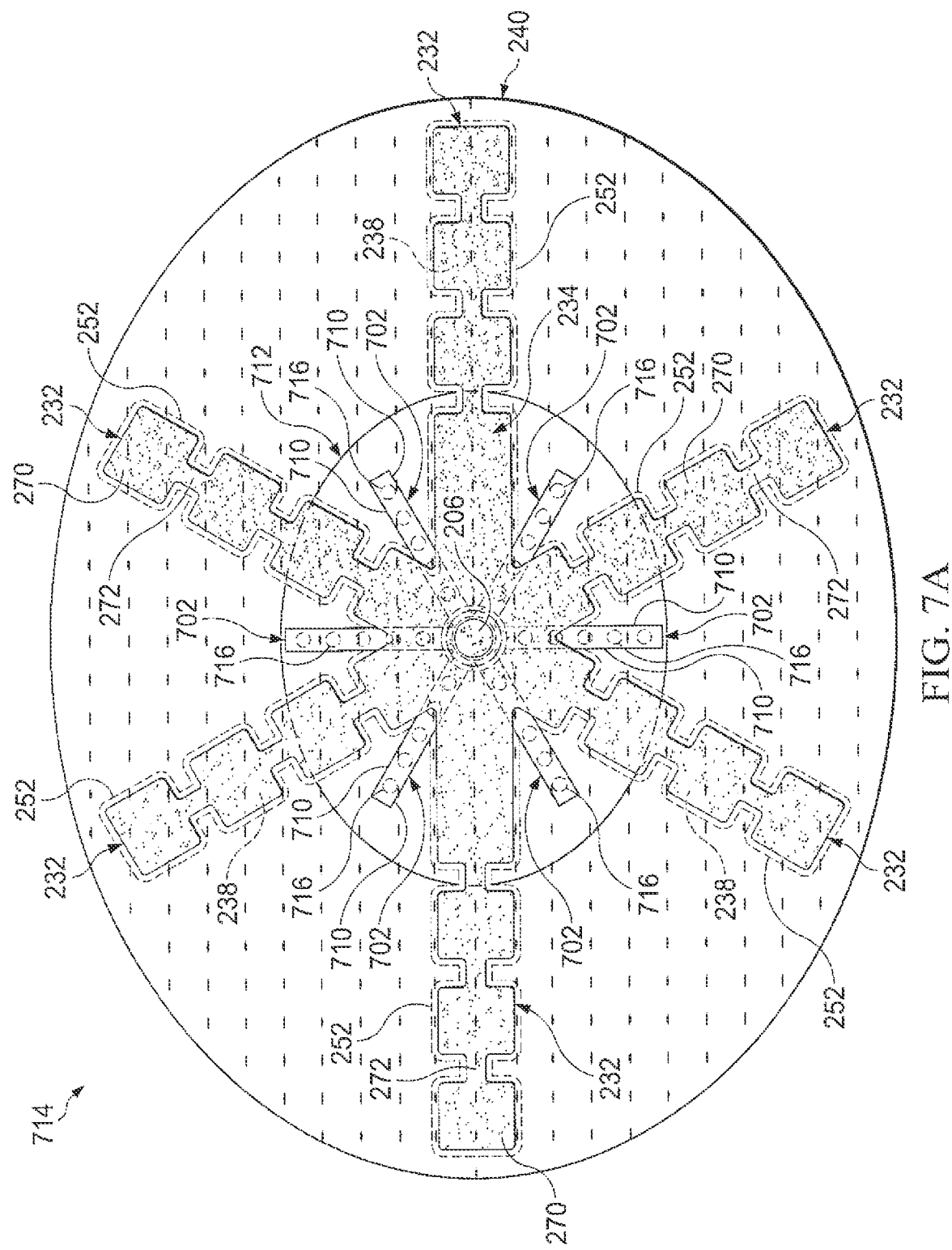
FIG. 7A is a top, plan view of another illustrative embodiment of a dressing suitable for use with the treatment system of FIG. 1.
Figure 7B:
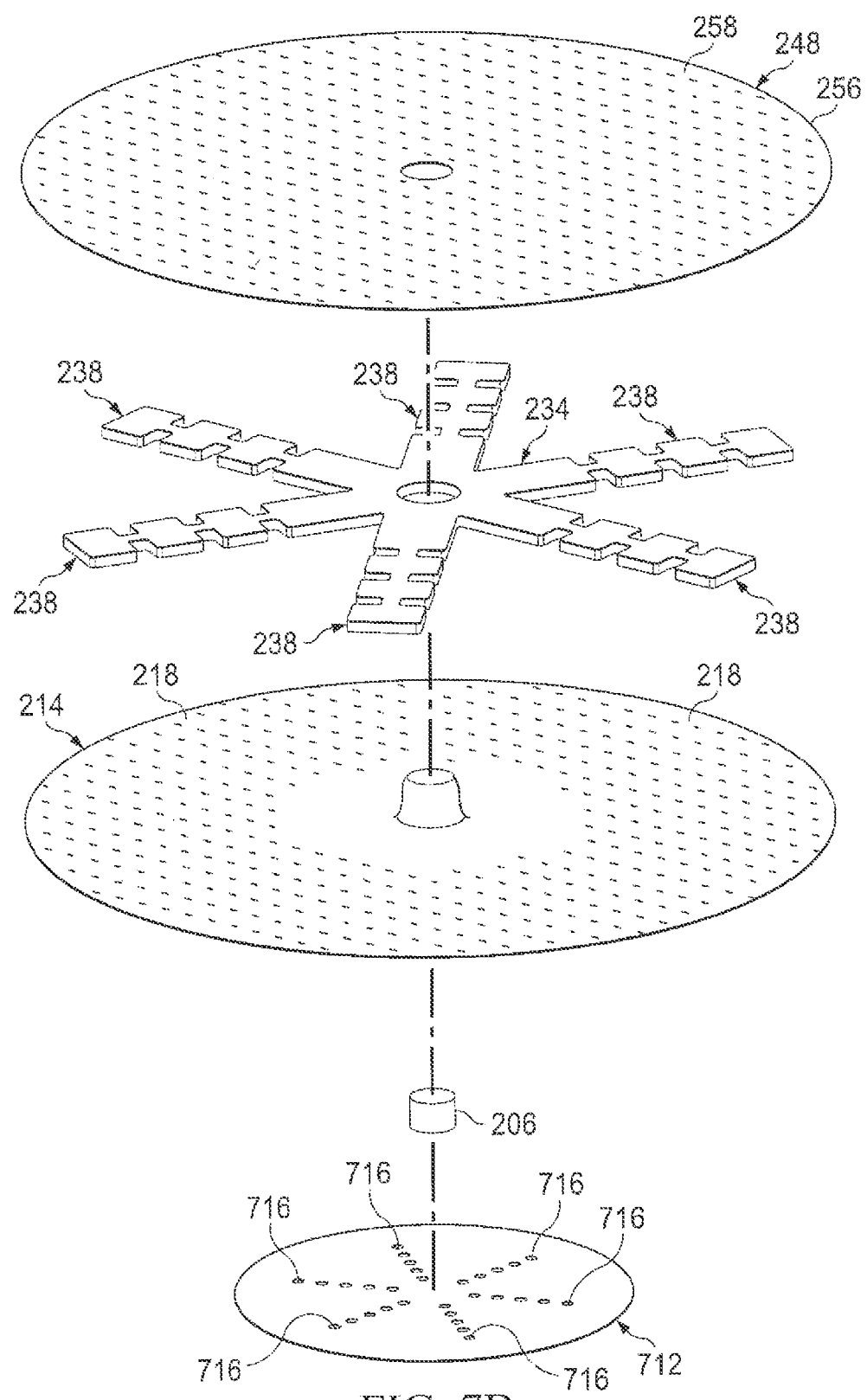
FIG. 7B is an exploded, perspective view of another illustrative embodiment of an instillation assembly and a reduced-pressure assembly depicted in FIG. 7A.

Referring to FIGS. 7A-7B, provided is another illustrative embodiment of a dressing 714 suitable for use with the treatment system 102. The dressing 714 may include similar components having similar structure and operation as the dressing 114, and thus, the same element numbers appearing in FIGS. 7A-7B may refer to the same components of the dressing 114.

Compared to the dressing 114, the dressing 714 may omit the first encapsulating layer 246. Further, the dressing 714 may include a first film layer 712 that may be smaller in size than the than the second film layer 214, and may be free of the film fenestrations 218 described in connection with the dressing 114. For example, the first film layer 712 may have, without limitation, a smaller diameter, perimeter, or circumference than the second film layer 214 such that a periphery of the second film layer 214 is adapted to extend beyond a periphery of the first film layer 712. In such a configuration, when the first film layer 712 is coupled or positioned relative to the second film layer 214 as described herein, the film fenestrations 218 and the second film layer 214 may be positioned in direct fluid communication or contact with the tissue site 116. Similar to the first film layer 212, the first film layer 712 may be adapted to face the tissue site 116, and may comprise similar materials as those recited above for the first film layer 212.

Further, the dressing 714 may include a plurality of fluid distribution lumens 702 and a plurality of delivery apertures 716. The fluid distribution lumens 702 may have a straight longitudinal shape with opposing sides 710 that differs from the previously described fluid distribution lumens 202. The first film layer 712 may be sealingly coupled to the second film layer 214 at the opposing sides 710 to form the fluid distribution lumens 702 analogous to the fluid distribution lumens 202. Similarly, the delivery apertures 716 may be positioned along a common longitudinal axis that differs from the positioning of the delivery apertures 216. However, the fluid distribution lumens 702 and the delivery apertures 716 may otherwise be analogous in operation to the fluid distribution lumens 202 and the delivery apertures 216, respectively.

Continuing with FIGS. 7A-7B, also provided is another illustrative embodiment of a method of manufacturing the dressing 714 for use with the treatment system 102 in treating the tissue site 116. In some embodiments, the leg encapsulating material 240 may include the second film layer 214 and the second encapsulating layer 248, and the method may include positioning the leg manifold 238 between the second film layer 214 and the second encapsulating layer 248, and coupling the second film layer 214 to the second encapsulating layer 248 around the leg manifold 238. The leg bond 252 may couple the second film layer 214 to the second encapsulating layer 248 without crossing into the distribution lumens 702. In some embodiments, the first film layer 712 may be coupled to the second film layer 214 for defining the plurality of fluid distribution lumens 702 before coupling the second film layer 214 to the second encapsulating layer 248 around the leg manifold 238.

Figure 8A:
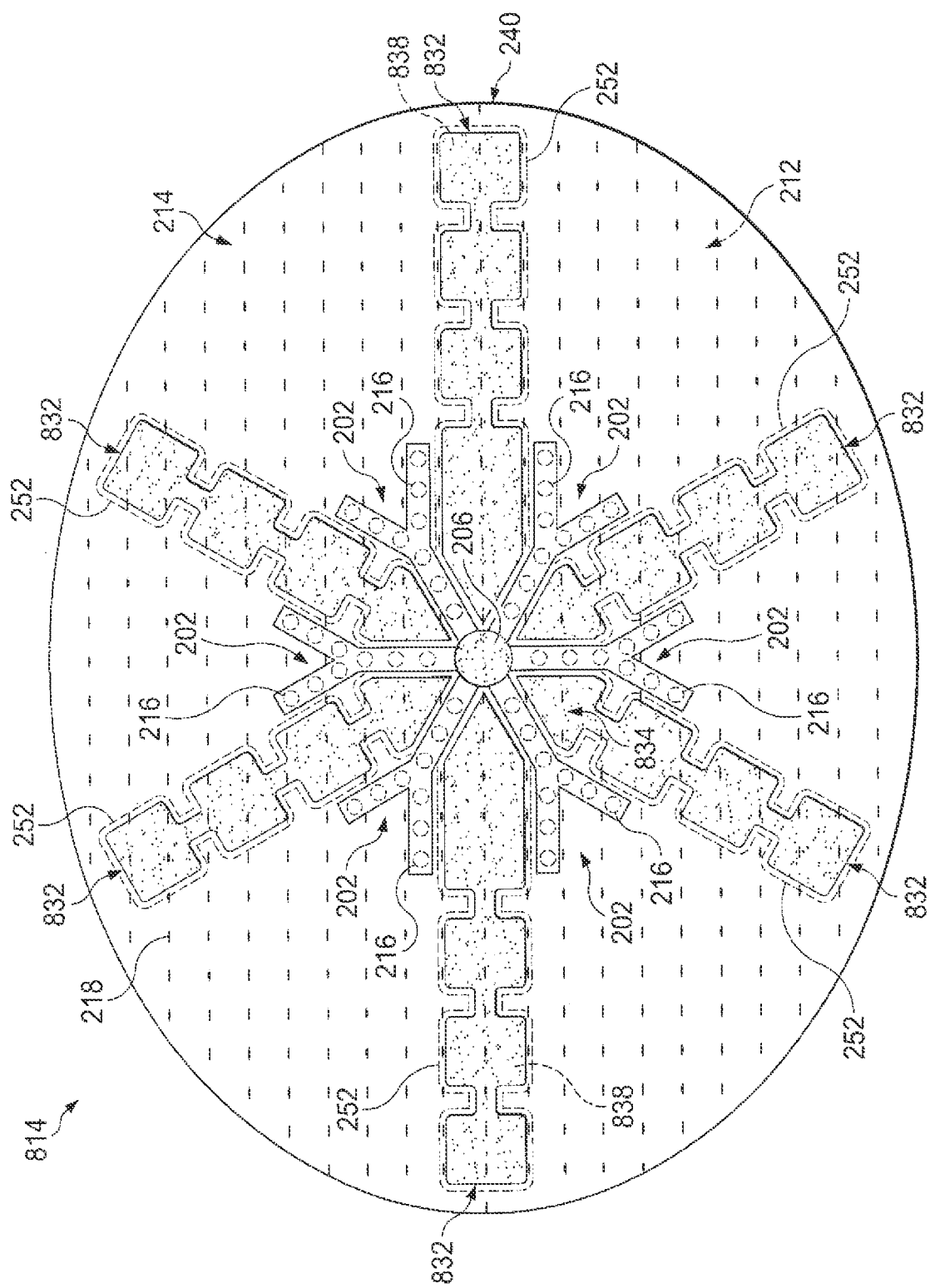
FIG. 8A is a top, plan view of another illustrative embodiment of a dressing suitable for use with the treatment system of FIG. 1.
Figure 8B:
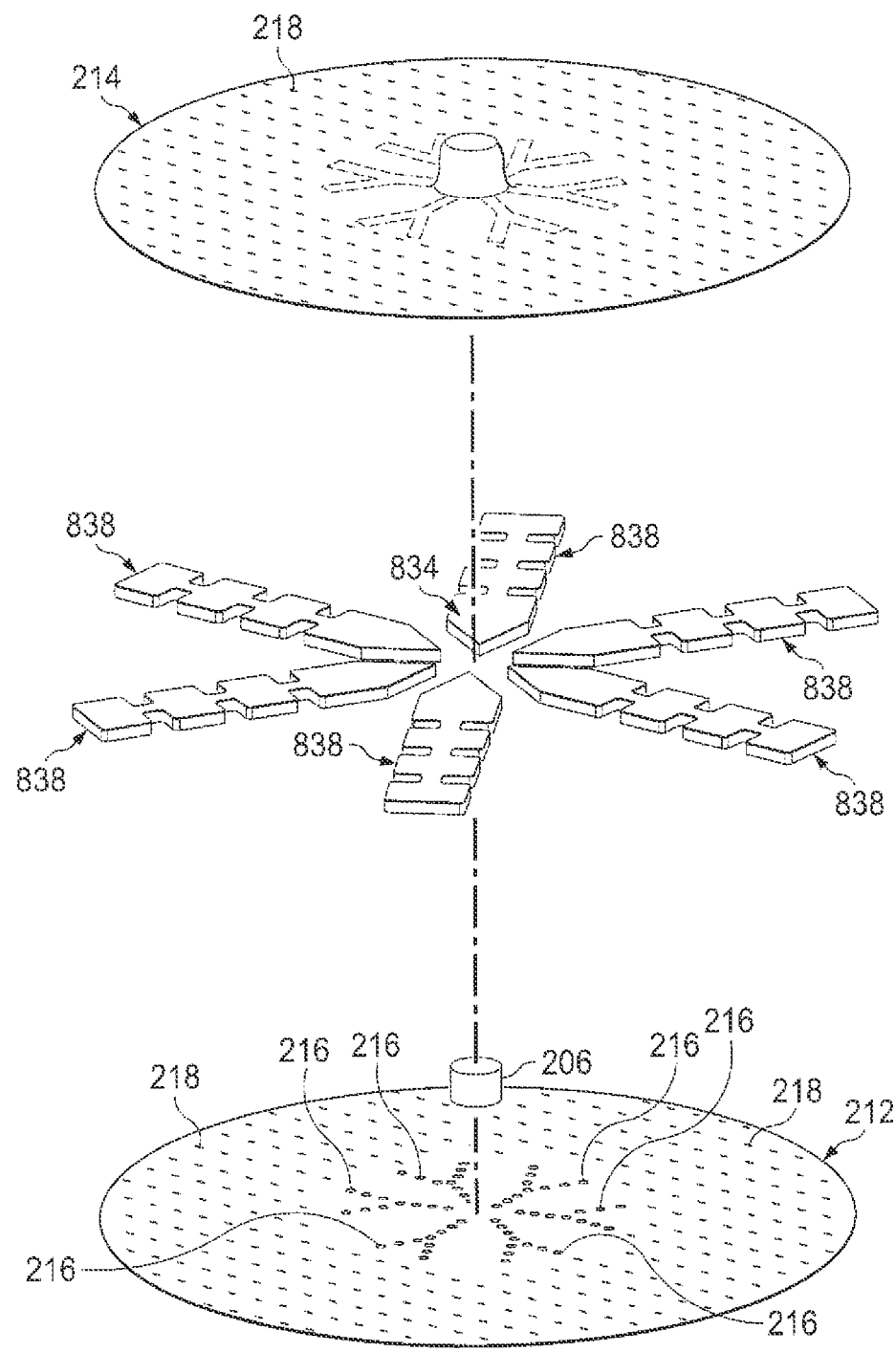
FIG. 8B is an exploded, perspective view of another illustrative embodiment of an instillation assembly and a reduced-pressure assembly depicted in FIG. 8A.

Referring to FIGS. 8A-8B, provided is another illustrative embodiment of a dressing 814 suitable for use with the treatment system 102. The dressing 814 may include similar components having similar structure and operation as the dressing 114, and thus, the same element numbers appearing in FIGS. 8A-8B may refer to the same components of the dressing 114.

Compared to the dressing 114, the dressing 814 may omit the first encapsulating layer 246 and the second encapsulating layer 248. Further, the dressing 814 may include a plurality of leg members 832 and a reduced-pressure hub 834 that may be analogous in operation to the leg members 232 and the reduced-pressure hub 234, respectively, of the dressing 114. However, as shown, the leg members 832 may be gathered at or oriented toward the reduced-pressure hub 834 without being coupled together or formed from a continuous piece of material. Each of the leg members 832 may include a leg manifold 838 and the leg encapsulating material 240. The leg manifold 838 may be comprised of any of the materials recited above for the leg manifold 238. Although the leg members 832 may be gathered rather than coupled at the reduced-pressure hub 834, when the dressing 814 is positioned at the tissue site 116 with the distribution manifold 108 in a manner analogous to the dressing 114, the distribution manifold 108 may overlap the leg members 832 at the reduced-pressure hub 834 for providing or enhancing fluid communication among the leg members 832.

Continuing with FIGS. 8A-8B, also provided is another illustrative embodiment of a method of manufacturing the dressing 814 for use with the treatment system 102 in treating the tissue site 116. In some embodiments, the leg encapsulating material 240 may be the first film layer 212 and the second film layer 214, and the method may include positioning the leg manifold 838 between the first film layer 212 and the second film layer 214, and coupling the first film layer 212 to the second film layer 214 around the leg manifold 838. The leg bond 252 may couple the first film layer 212 to the second film layer 214 without crossing into the distribution lumens 202.

Although this specification discloses advantages in the context of certain illustrative, non-limiting embodiments, various changes, substitutions, permutations, and alterations may be made without departing from the scope of the appended claims. Further, any feature described in connection with any one embodiment may also be applicable to any other embodiment.

What is claimed is:

1. A treatment system for providing fluid instillation and reduced-pressure treatment at a tissue site, comprising:
   a plurality of fluid distribution lumens, each fluid distribution lumen being formed by a first film layer being sealingly coupled to a second film layer along a length and opposing sides, the opposing sides being positioned substantially normal to the length, each of the fluid distribution lumens having a delivery aperture;
   a fluid hub positioned in fluid communication with the plurality of fluid distribution lumens, the fluid hub extending outward from a surface of the second film layer, the fluid hub and the plurality of fluid distribution lumens defining a fluid instillation pathway;
   a plurality of leg members;
   a reduced-pressure hub in fluid communication with the plurality of leg members, the reduced-pressure hub and the plurality of leg members defining a reduced-pressure pathway separate from the fluid instillation pathway;
   a fluid supply lumen adapted to be coupled in fluid communication with the fluid hub; and
   a reduced-pressure lumen adapted to be coupled in fluid communication with the reduced-pressure hub.

2. The treatment system of claim 1, wherein the first film layer is adapted to face the tissue site, and wherein the delivery aperture in each of the fluid distribution lumens is disposed through the first film layer.

3. The treatment system of claim 1, wherein the fluid hub is positioned between the first film layer and the second film layer.

4. The treatment system of claim 1, wherein each of the leg members comprises a leg manifold and a leg encapsulating material, the leg manifold being encapsulated by the leg encapsulating material, a plurality of leg fenestrations being disposed through the leg encapsulating material in fluid communication with the leg manifold.

5. The treatment system of claim 4, wherein each of the leg members comprises an interior and an exterior defined by the leg encapsulating material, the leg manifold being positioned within the interior of the leg member, the plurality of leg fenestrations being disposed through the leg encapsulating material in fluid communication between the leg manifold and the exterior of the leg member.

6. The treatment system of claim 1, wherein the first film layer and the second film layer are adapted to separate the plurality of fluid distribution lumens and the fluid hub from the plurality of leg members and the reduced-pressure hub.

7. The treatment system of claim 1, further comprising a central opening disposed through the reduced-pressure hub and adapted to receive the fluid hub, the fluid hub having a height adapted to extend through the central opening.

8. The treatment system of claim 1, wherein the plurality of fluid distribution lumens are adapted to be positioned between the tissue site and the plurality of leg members.

9. The treatment system of claim 1, further comprising a dressing sealing member adapted to cover the tissue site and to provide a sealed space between the dressing sealing member and the tissue site, the plurality of fluid distribution lumens and the plurality of leg members adapted to be positioned in the sealed space.

10. The treatment system of claim 9, further comprising a distribution manifold for positioning in the sealed space between the sealing member and the plurality of leg members.

11. The treatment system of claim 10, wherein the distribution manifold is adapted to distribute reduced pressure to the plurality of leg members.

12. The treatment system of claim 10, wherein the distribution manifold is adapted to be positioned adjacent to the reduced-pressure hub, and wherein the distribution manifold is adapted to distribute reduced pressure to the plurality of leg members through at least the reduced-pressure hub.

13. The treatment system of claim 10, wherein the distribution manifold comprises a distribution manifold opening disposed through the distribution manifold and adapted to receive the fluid hub, the fluid hub having a height adapted to extend through the distribution manifold opening.

14. The treatment system of claim 1, wherein the fluid supply lumen is adapted to be coupled in fluid communication with the fluid hub at a fluid supply connection, and wherein the reduced-pressure lumen is adapted to be coupled in fluid communication with the reduced-pressure hub at a reduced-pressure connection, the fluid supply connection being fluidly isolated from the reduced-pressure connection.

15. The treatment system of claim 1, wherein the reduced-pressure lumen is fluidly isolated from the fluid supply lumen.

16. The treatment system of claim 1, wherein the reduced-pressure lumen has a length fluidly isolated from an entire length of the fluid supply lumen.

17. The treatment system of claim 1, further comprising a distribution manifold adapted to be positioned adjacent to the reduced-pressure hub, wherein the reduced-pressure lumen is adapted to be coupled in fluid communication with the reduced-pressure hub through the distribution manifold.

18. The treatment system of claim 1, further comprising a reduced-pressure source for coupling in fluid communication with the reduced-pressure lumen.

19. The treatment system of claim 1, further comprising a positive-pressure source for coupling in fluid communication with the fluid supply lumen.

20. The treatment system of claim 19, further comprising a fluid instillation reservoir positioned in fluid communication with the positive-pressure source, the positive-pressure source adapted to be coupled in fluid communication with the fluid supply lumen through the fluid instillation reservoir.

21. The treatment system of claim 1, the plurality of fluid distribution lumens being positioned circumferentially and substantially symmetric about the fluid hub.

22. The treatment system of claim 1, wherein each of the fluid distribution lumens comprise a plurality of delivery apertures disposed through the first film layer, the plurality of delivery apertures of each of the fluid distribution lumens being equal in number and size.

23. The treatment system of claim 1, wherein each of the fluid distribution lumens is adapted to provide substantially the same back-pressure.

24. The treatment system of claim 1, wherein at least a portion of the first film layer is hydrophilic.

25. The treatment system of claim 1, wherein each of the fluid distribution lumens has an internal diameter between about 2 millimeters to about 6 millimeters.

* * * * *

UNITED STATES PATENT AND TRADEMARK OFFICE
CERTIFICATE OF CORRECTION

Page 1 of 1

PATENT NO. : 10,702,649 B2
APPLICATION NO. : 15/328415
DATED : July 7, 2020
INVENTOR(S) : Mercer et al.

It is certified that error appears in the above-identified patent and that said Letters Patent is hereby corrected as shown below:

On the Title Page

<u>On Page 3, Column 1, item (56) Under (Other Publications)</u>
Line 7, delete "Philidelphia," and insert -- Philadelphia, --, therefor.

<u>On Page 3, Column 2, item (56) Under (Other Publications)</u>
Line 42, delete "Radek," and insert -- Radak, --, therefor.
Line 62, delete "Hypermia" and insert -- Hyperemia --, therefor.

In the Specification

<u>Column 3</u>
Line 59, delete "may be may be" and insert -- may be --, therefor.

<u>Column 7</u>
Line 41, delete "Expopack" and insert -- Exopack --, therefor.
Line 54, delete "Expopack" and insert -- Exopack --, therefor.

Signed and Sealed this
Thirty-first Day of August, 2021

Drew Hirshfeld
*Performing the Functions and Duties of the*
*Under Secretary of Commerce for Intellectual Property and*
*Director of the United States Patent and Trademark Office*